United States Patent
Inghardt et al.

(10) Patent No.: US 11,000,525 B2
(45) Date of Patent: *May 11, 2021

(54) 1-[2-(AMINOMETHYL)BENZYL]-2-THIOXO-1,2,3,5-TETRAHYDRO-4H-PYRROLO[3,2-D] PYRIMIDIN-4-ONES AS INHIBITORS OF MYELOPEROXIDASE

(71) Applicant: AstraZeneca AB, Sodertalje (SE)

(72) Inventors: Tord Bertil Inghardt, Mölndal (SE); Petra Johannesson, Mölndal (SE); Ulrik Jurva, Mölndal (SE); Erik Michaelsson, Mölndal (SE); Eva-Lotte Lindstedt-Alstermark, Mölndal (SE); Nicholas Tomkinson, Macclesfield (GB); Jeffrey Paul Stonehouse, Waltham, MA (US); Li-Ming Gan, Mölndal (SE)

(73) Assignee: ASTRAZENECA AB, Sodertalje (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/009,590

(22) Filed: Jun. 15, 2018

(65) Prior Publication Data
US 2019/0076432 A1    Mar. 14, 2019

Related U.S. Application Data

(63) Continuation of application No. 15/454,318, filed on Mar. 9, 2017, now Pat. No. 10,016,430, which is a
(Continued)

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01)

(58) Field of Classification Search
CPC ........................... A61K 31/519; C07D 487/04
(Continued)

(56) References Cited

U.S. PATENT DOCUMENTS 9,249,087 B2   2/2016  Bergman et al.
9,616,063 B2 * 4/2017  Inghardt ............... A61K 31/519
10,016,430 B2 * 7/2018  Inghardt ............... A61K 31/519

FOREIGN PATENT DOCUMENTS

WO   03089430 A1   10/2003
WO   2005037835 A1   4/2005
(Continued)

OTHER PUBLICATIONS

Anderson, Chemistry & Biology 2003, vol. 10, pp. 787-797. (Year: 2003).*
(Continued)

*Primary Examiner* — Craig D Ricci
*Assistant Examiner* — Janet L. Coppins

(57) ABSTRACT

There are disclosed certain 1-[2-(aminomethyl)benzyl]-2-thioxo-1,2,3,5-tetrahydro-4H-pyrrolo[3,2-d]pyrimidin-4-one compounds of formula (I),
(Continued)

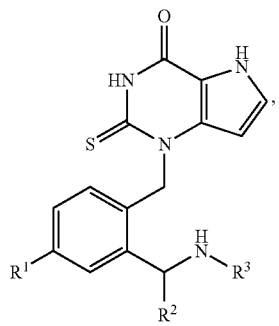

(I)

and pharmaceutically acceptable salts thereof, together with compositions containing them and their use in therapy. The compounds are inhibitors of the enzyme MPO and are thereby particularly useful in the treatment or prophylaxis of cardiovascular disorders such as heart failure and coronary artery disease related conditions.

2 Claims, 6 Drawing Sheets

Related U.S. Application Data continuation of application No. 14/951,979, filed on Nov. 25, 2015, now Pat. No. 9,616,063.

(60) Provisional application No. 62/166,808, filed on May 27, 2015, provisional application No. 62/085,722, filed on Dec. 1, 2014.

(58) Field of Classification Search
USPC .................................. 514/265.1; 544/280
See application file for complete search history.

(56) References Cited

FOREIGN PATENT DOCUMENTS

| WO | | 2006062465 | A1 | | 6/2006 | | |
|---|---|---|---|---|---|---|---|
| WO | WO | 2006062465 | A1 | * | 6/2006 | ........... | C07D 487/04 |
| WO | | 2007120097 | A1 | | 10/2007 | | |
| WO | | 2007120098 | A1 | | 10/2007 | | |
| WO | | 2007142576 | A1 | | 12/2007 | | |
| WO | | 2007142577 | A1 | | 12/2007 | | |
| WO | | 2009025618 | A1 | | 2/2009 | | |
| WO | | 2012106343 | A2 | | 8/2012 | | |
| WO | | 2013068875 | A1 | | 5/2013 | | |

OTHER PUBLICATIONS

Thiel, Nature Biotechnology 2004, vol. 22(5), pp. 513-519. (Year: 2004).*
https://www.who.int/news-room/fact-sheets/detail/cardiovascular-diseases-(cvds), dated May 17, 2017. (Year: 2017).*
Malmquist et al., "Imaging agents for myeloperoxidase," Journal of Labelled Compounds and Radiopharmaceuticals, 2012, 55, pp. 393-399.
Tiden et al., "2-Thioxanthines are mechanism-based inactivators of myeloperoxidase that block oxidative stress during inflammation," The Journal of Biological Chemistry, vol. 286, No. 43, pp. 37578-37589, Oct. 28, 2011.
International Search Report issued for PCT/EP2015/077998 dated Jan. 2, 2016.
Written Opinion issued for PCT/EP2015/077998 dated Jan. 2, 2016.

* cited by examiner

| | MPO act | Calprotectin | Allantoin | MPO mass | Arg/ADMA | Endothelin-1 | TIMP-4 | sTNFR-1 | NGAL | OPN | TIMP-1 | Urate |
|---|---|---|---|---|---|---|---|---|---|---|---|---|
| MPO activity | | 0.11 | 0.013 | 0.046 | 0.18 | 0.00055 | 0.021 | 0.094 | 0.11 | 0.40 | 0.20 | 0.0308 |
| Calprotectin | | | 0.011 | 0.000045 | 0.0013 | 0.069 | 0.067 | 0.00011 | 0.00084 | 0.14 | 0.022 | 0.0252 |
| Allantoin | | | | 0.000054 | 0.0019 | 0.000026 | 0.031 | 0.0011 | 0.0028 | 0.20 | 0.035 | 0.0043 |
| MPO mass | | | | | 0.012 | 0.0007 | 0.15 | 0.090 | 0.10 | 0.11 | 0.036 | 0.0057 |
| Arg/ADMA | | | | | | 0.000011 | 0.041 | 0.00056 | 0.014 | 0.089 | 0.00042 | 0.00092 |
| Endothelin-1 | | | | | | | 0.0028 | 0.099 | 0.49 | 0.29 | 0.0000016 | 0.0027 |
| TIMP-4 | | | | | | | | 0.000073 | 0.00092 | 0.23 | 0.0011 | 0.00029 |
| sTNFR-1 | | | | | | | | | 7.9E-31 | 0.00069 | 0.0000035 | 0.0013 |
| Lipocalin-2 | | | | | | | | | | 0.0011 | 0.0056 | 0.0013 |
| OPN | | | | | | | | | | | 0.033 | 0.0499 |
| TIMP-1 | | | | | | | | | | | | 0.019 |

1-[2-(AMINOMETHYL)BENZYL]-2-THIOXO-1,2,3,5-TETRAHYDRO-4H-PYRROLO[3,2-D]PYRIMIDIN-4-ONES AS INHIBITORS OF MYELOPEROXIDASE

This application is a continuation of U.S. application Ser. No. 15/454,318 filed on Mar. 9, 2017, said application Ser. No. 15/454,318 is a continuation of U.S. application Ser. No. 14/951,979 filed on Nov. 25, 2015, which claims benefit under 35 U.S.C. § 119(e) of the following U.S. Provisional Application No. 62/085,722, filed Dec. 1, 2014, and U.S. Provisional Application No. 62/166,808, filed May 27, 2015. Each of the above listed applications is incorporated by reference herein in its entirety for all purposes.

TECHNICAL FIELD

The technical field relates to certain 1-[2-(aminomethyl)benzyl]-2-thioxo-1,2,3,5-tetrahydro-4H-pyrrolo[3,2-d]pyrimidin-4-one compounds of formula (I), to their use in the treatment of a myeloperoxidase related disease or condition, for example heart failure and coronary artery disease related conditions, and to pharmaceutical compositions containing them.

BACKGROUND

Myeloperoxidase (MPO) is a heme-containing enzyme found in neutrophilic granulocytes (neutrophils) and monocytes. MPO is one member of a diverse protein family of mammalian peroxidases that also includes eosinophil peroxidase (EPO), thyroid peroxidase (TPO), salivary peroxidase (SPS), lactoperoxidase (LPO), prostaglandin H synthase (PGHS), and others. The mature enzyme is a dimer of identical halves. Each half molecule contains a covalently bound heme that exhibits unusual spectral properties responsible for the characteristic green color of MPO. Cleavage of the disulphide bridge linking the two halves of MPO yields the hemi-enzyme that exhibits spectral and catalytic properties indistinguishable from those of the intact enzyme. The enzyme is activated by hydrogen peroxide, the source of which can be superoxide dismuatase (SOD)-catalyzed NADPH-derived superoxide anion and xanthine oxidase-derived superoxide anion and hydrogen peroxide formed upon purine oxidation. The main physiological substrates of MPO are halides (e.g. chloride) and pseudohalides (like thiocyanate), forming microbicidal hypohalous acids like hypochlorous acid (bleach) and hypothiocyanous acid (*J. Clin. Biochem. Nutr.*, 2011, 48, 8-19).

Neutrophils play an important microbicidal role by phagocytosing (engulfing) and killing microorganisms. The engulfed load is incorporated into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound (*Free Radical Biology & Medicine*, 2010, 49, 1834-1845). Hypochlorous acid is oxidizing in itself, and reacts most avidly with thiols and thioethers, but also converts amines into chloramines, and chlorinates aromatic amino acids.

MPO can also be released to the outside of the cells where the reaction with chloride can induce damage to adjacent tissue. In addition to this controlled release of MPO, neutrophils can also cast webs of decondensed DNA interspersed with intracellular proteins such as MPO into the extracellular space, so called neutrophil extracellular traps (NET). These NETs are thought to play a role in host defense towards extracellular microbes and has also been suggested to be an important pathophysiological mechanism in acute inflammatory diseases such as the immunothrombosis occurring in sepsis (*Nature Rev. Immunol*, 2013, 13, 34) and in autoimmunity, such as in systemic lupus erythematosus (SLE)(*J. Immunol.*, 2011, 187, 538-552). Notably, MPO is required for NET formation (*Blood*, 2011, 117, 953).

Systemic levels of MPO is a well-described risk factor for various cardiovascular diseases (e.g. heart failure, acute coronary syndrome, myocardial infarction, stable coronary artery disease and atherosclerosis related conditions (*Circulation*, 2003, 108, 1440-1445; N. *Engl. J. Med.*, 2003, 349, 1595-604; *J. Am. Coll. Cardiol.*, 2007, 49, 2364-70). The role of MPO in these morbidities is not only related to the oxidative damage caused by the enzymatic products, but also a due to a consumption of nitric oxide, an important regulator of vascular and cardiomyocyte relaxation. Importantly, the contribution of MPO to cardiovascular diseases is not only via infiltration of neutrophils and monocytes into the vasculature and the myocardium, but also via the strategic deposition of extracellular MPO on proteoglycans on the basolateral side of the endothelium (*Science*, 2002, 296, 2391).

A causative role of MPO for the development of cardiovascular disease is also supported by the lower cardiovascular morbidity in MPO-defective subjects (*Acta Haematol.*, 2000, 104, 10-15) and reduced coronary flow reserve (*J. Biomed. Sci.*, 2004, 11, 59-64) and increased mortality in subjects carrying a gain-of-function mutation in the MPO-promotor (*New Engl. J. Med.*, 2004, 350, 517; *Free Rad. Biol. & Med.*, 2009, 47, 1584; *J. Biol. Chem.*, 1996, 271, 14412-14420). A direct effect on vascular flow and relaxation was also observed after administration of MPO in pigs (*Eur. Heart J.*, 2011, 33, 1625).

Linkage of MPO activity to diseases has thus been implicated in cardiovascular diseases with microvascular inflammation and reactive fibrosis including heart failure such as heart failure with preserved ejection fraction, heart failure with reduced ejection fraction, acute coronary syndrome, myocardial infarction, stable coronary artery disease and atherosclerosis related conditions.

Although considerable progress has been made in the understanding and treatment of heart failure (HF), morbidity and mortality due to HF remain high. The main cause of cardiac remodeling, which underlies HF development, is increased ventricular wall stress as a result of sustained hypertension, myocardial infarction, valvular insufficiency or other events. Cardiac remodeling is referred to as any change in cardiac structure, dimension, mass or function and, although it is initially a compensatory mechanism to maintain cardiac output it may result in decompensation and HF development (*J. Am. Coll. Cardiol.*, 2000, 35, 569-582). Main processes that contribute to cardiac remodeling are cardiomyocyte hypertrophy (growth), fibrosis and inflammation (*Nat. Rev. Mol. Cell. Biol.*, 2006, 7, 589-600; *Circ. Res.*, 2010, 106, 47-57).

Currently, the cornerstone of HF treatment is based on reduction of ventricular wall stress and it consists mainly on the use of inhibitors of the renin-angiotensin-aldosterone systems, such as angiotensin-converting enzyme-inhibitors (ACE-I), of β-adrenergic blockers and of diuretics (*Eur. Heart J.*, 2012, 14, 803-869). Despite treatment, HF mortality is still high and about 50% of all patients die within 5 years after first diagnosis (*J. Am. Coll. Cardiol.*, 1999, 33, 734-742). New treatment options directly focused at the major molecular and cellular processes driving cardiac remodeling are therefore urgently needed.

Heart failure can be sub-divided in HF with reduced ejection fraction (HFrEF) and with preserved ejection fraction (HFpEF) (*Curr. Heart Fail. Rep.*, 2012, 9, 363-368). HFrEF and HFpEF differ with regard to pathophysiology, clinical characteristics and treatment. HFrEF is often referred to as systolic HF and treatment with ACE inhibitors, β-blockers and diuretics have successfully reduced mortality and morbidity rates in patients with HFrEF. In contrast, for HFpEF, which is often denoted as diastolic HF, no treatment has to date convincingly shown to reduce mortality or morbidity. This is alarming, since the incidence and prevalence of HFpEF is rising, both in absolute terms and relative to HFrEF (*Eur. Heart J.*, 2013, 34, 1424-1431). A key characteristic of HFpEF is reduced contractility and relaxation of the ventricular wall. Cardiac fibrosis is an important contributor of this stiffening of the ventricular wall. Targeting cardiac fibrosis is therefore an potential therapeutic strategy for HFpEF patients, but also in HFrEF patients fibrosis plays an important role. Moreover, HFpEF may transit into cardiac dilatation and into HFrEF. It will therefore be important to investigate whether pharmacological targeting of cardiac fibrosis could halt or attenuate HFpEF and its potential transition into HFrEF. Microvascular inflammation, resulting in interstitial fibrosis appears to play an important role in HFpEF development (*J. Am. Coll. Cardiol.*, 2013, 62, 263-271) and an association has been demonstrated between HF and the inflammatory enzyme, myeloperoxidase (MPO)(*J. Am. Coll. Cardiol.*, 2007, 49, 2364-2370). In terms of fibrosis, there are data suggesting that the MPO-product hypochlorous acid (HOCl), is an important regulatory switch modulating extracellular matrix proteins, including metalloproteinases (MMPs) (*J. Biol. Chem.*, 2001, 276, 4127941287; *J. Biol. Chem.*, 2003, 278, 28403-28409). This is also supported by the attenuation of angiotensin II-induced atrial fibrosis and reduced MMP-activity observed in MPO-deficient. Moreover, addition of recombinant MPO to Mpo−/− mice resulted in atria fibrosis indicating that increased MPO activity is sufficient for induction of fibrosis (*Nat. Med.*, 2010, 16, 470-474). In a post-myocardial infarct (MI) model Mpo−/− mice also showed diminished ventricular remodeling and improved function (*J. Exp. Med.*, 2003, 197, 615-624). Together these results indicate that MPO activity is a key player for structural remodeling of the myocardium under pathological conditions.

Pharmacological inhibition of MPO activity could attenuate cardiac fibrosis and preserve cardiac function under conditions that may trigger (diastolic) HFpEF and (systolic) HFrEF. In particular stiffening of the heart as a result of extensive fibrosis could be prevented and may preserve cardiac function.

There is a need for an orally active inhibitor of MPO for the treatment of e.g. heart failure and coronary artery disease related conditions. In order to increase the therapeutic index of such a medication, it is necessary to obtain an MPO inhibitor being selective for MPO over other peroxidases such as for instance TPO to reduce the risk of thyroid related adverse events. It is considered that a high selectivity for MPO over TPO may reduce the risk of a growth of the thyroid gland (*Pharm. Res.*, 2013, 30, 1513-24. Furthermore, it is desirable that an MPO inhibitor for the use in cardiovascular therapy would have limited blood brain barrier penetrating properties as to minimize its effect in the central nervous system (CNS).

WO2003/089430, WO2005/037835, WO2007/120097, WO2007/120098 and WO2007/142576 disclose thioxantine derivatives and the use thereof as MPO inhibitors in therapy.

WO2006/062465 and WO2007/142577 disclose 2-thioxo-1,2,3,4-tetrahydro-pyrrolo[3,2-d]pyrimidin-4-one derivatives claimed to be inhibitors of MPO. It is stated that the compounds may show selectivity against related enzymes such as TPO.

WO2009/025618 discloses thioxantine and 2-thioxo-1,2, 3,4-tetrahydro-pyrrolo[3,2-d]pyrimidin-4-one derivatives and the use of MPO inhibitors for the treatment of multiple system atrophy (MSA) and Huntington's disease (HD) and for neuroprotection.

*J. Labelled Compounds and Radiopharmaceuticals*, 2012, 55, 393-399, discloses some tritiated, $^{13}C$ and $^{14}C$ labeled thioxantine derivatives as well as a $^{14}C$ labeled pyrrolo[3,2-d]pyrimidin-4-one compound. The compounds are stated to be inactivators of MPO.

*J. Biol. Chem.*, 2011, 286, 37578-37589, discloses certain thioxantine derivatives. The compounds are stated to inhibit MPO in plasma and decrease protein chlorination in a mouse model. The compounds are also claimed to be poor inhibitors of TPO.

WO2013/068875 discloses thiopyrimidone derivatives claimed to be MPO inhibitors.

An object is to provide novel MPO inhibitors useful in therapy. A further object is to provide novel compounds having improved selectivity for the MPO enzyme over the TPO enzyme and/or having limited blood brain barrier penetrating properties.

SUMMARY

There is provided a compound of formula (I).

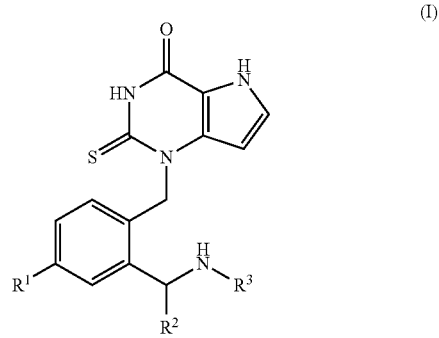

wherein
$R^1$ is H, F, Cl or CF$_3$,
$R^2$ is H, CH$_3$ or C$_2$H$_5$, and
$R^3$ is H, CH$_3$, C$_2$H$_5$, n-propyl, isopropyl, n-butyl, isobutyl, sec-butyl, tert-butyl, cyclopropyl, cyclopropylmethyl, cyclobutyl, cyclobutylmethyl or cyclopentyl, or a pharmaceutically acceptable salt thereof.

The compounds of formula (I) are MPO inhibitors. Thus, the compounds of formula (I) may be used as a medicament, in particular for disorders, diseases or conditions responsive to inhibition of MPO, and more specifically cardiovascular conditions, including coronary artery disease, heart failure (HF), heart failure with reduced ejection fraction (HFrEF) and heart failure with preserved ejection fraction (HFpEF), in which MPO plays a role.

It is to be understood that when the absolute configuration (R or S) of a single enantiomer of the compounds disclosed herein is specified in the present specification, it is the carbon atom to which $R^2$ is attached that is the stereocenter (chiral center) in question.

BRIEF DESCRIPTION OF THE DRAWINGS

FIG. 6 summarizes co-clustering of MPO-related biomarkers

DETAILED DESCRIPTION

Figure 1:
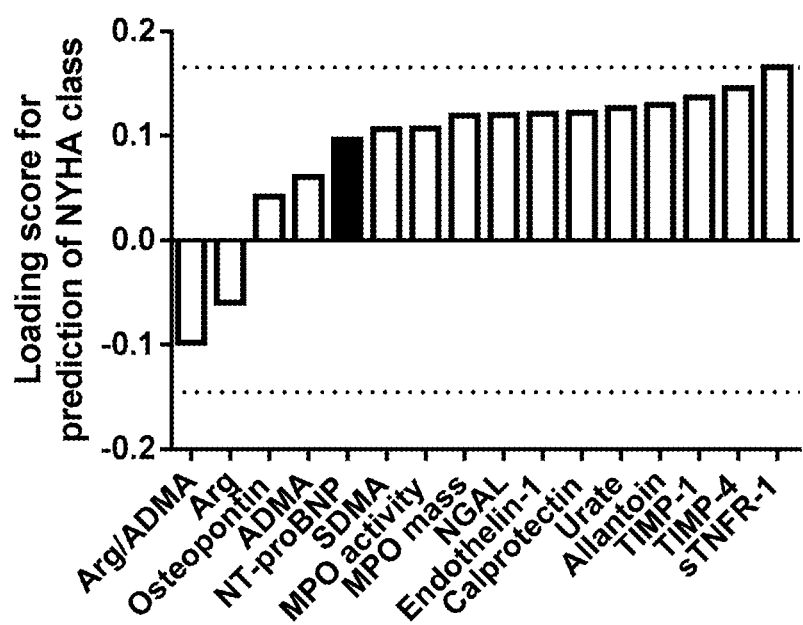
FIG. 1 shows the loading values of MPO-related biomarkers for prediction of symptomatic severity of HFpEF patients (NYHA class). For clarity, the loading values of the remaining variables (n=240) have been omitted in the figure. To put the shown loading values in perspective of the remainder of the data, the maximal and minimal loading values in the dataset are indicated by dotted lines. The black bar representing the loading value for NT-proBNP is shown for comparison.

For the avoidance of doubt it is to be understood that where in this specification a group is qualified by "defined above" the said group encompasses the first occurring and broadest definition as well as each and all of the other definitions for that group.

In one aspect, there are provided compounds of formula (I), or pharmaceutically acceptable salts thereof, wherein $R^1$ represents H, F, Cl or $CF_3$.

In a further embodiment, $R^1$ represents Cl.

In one embodiment, $R^2$ represents H, $CH_3$ or $C_2H_5$.

In a further embodiment, $R^2$ represents $CH_3$ or $C_2H_5$.

In still a further embodiment, $R^2$ represents $CH_3$.

In one embodiment, $R^3$ represents H, $CH_3$, $C_2H_5$, n-propyl, isopropyl, n-butyl, isobutyl, sec-butyl, tert-butyl, cyclopropyl, cyclopropylmethyl, cyclobutyl, cyclobutylmethyl or cyclopentyl.

In a further embodiment, $R^3$ represents H.

In still a further embodiment, the carbon atom to which $R^2$ is attached has the R-configuration when $R^2$ represents $CH_3$ or $C_2H_5$.

In one embodiment the compound of formula (I) is selected from:
1-{2-[(1R)-1-aminopropyl]-4-chlorobenzyl}-2-thioxo-1,2,3,5-tetrahydro-4H-pyrrolo[3,2-d]pyrimidin-4-one;
1-[2-(1-aminoethyl)-4-chlorobenzyl]-2-thioxo-1,2,3,5-tetrahydro-4H-pyrrolo[3,2-d]pyrimidin-4-one;
1-{2-[(1R)-1-aminoethyl]-4-chlorobenzyl}-2-thioxo-1,2,3,5-tetrahydro-4H-pyrrolo[3,2-d]pyrimidin-4-one;
1-{2-[(1S)-1-aminoethyl]-4-chlorobenzyl}-2-thioxo-1,2,3,5-tetrahydro-4H-pyrrolo[3,2-d]pyrimidin-4-one;
1-{4-chloro-2-[1-(methylamino)ethyl]benzyl}-2-thioxo-1,2,3,5-tetrahydro-4H-pyrrolo[3,2-d]pyrimidin-4-one;
1-{4-chloro-2-[(ethylamino)methyl]benzyl}-2-thioxo-1,2,3,5-tetrahydro-4H-pyrrolo[3,2-d]pyrimidin-4-one;
1-[2-(aminomethyl)-4-chlorobenzyl]-2-thioxo-1,2,3,5-tetrahydro-4H-pyrrolo[3,2-d]pyrimidin-4-one;
1-{4-chloro-2-[(methylamino)methyl]benzyl}-2-thioxo-1,2,3,5-tetrahydro-4H-pyrrolo[3,2-d]pyrimidin-4-one;
1-(2-{[(cyclobutylmethyl)amino]methyl}benzyl)-2-thioxo-1,2,3,5-tetrahydro-4H-pyrrolo[3,2-d]pyrimidin-4-one;
1-{2-[(cyclobutylamino)methyl]benzyl}-2-thioxo-1,2,3,5-tetrahydro-4H-pyrrolo[3,2-d]pyrimidin-4-one;
1-{2-[(cyclopentylamino)methyl]benzyl}-2-thioxo-1,2,3,5-tetrahydro-4H-pyrrolo[3,2-d]pyrimidin-4-one;
1-(2-{[(2-methylpropyl)amino]methyl}benzyl)-2-thioxo-1,2,3,5-tetrahydro-4H-pyrrolo[3,2-d]pyrimidin-4-one;
1-{2-[(propan-2-ylamino)methyl]benzyl}-2-thioxo-1,2,3,5-tetrahydro-4H-pyrrolo[3,2-d]pyrimidin-4-one;
1-[2-(aminomethyl)-4-(trifluoromethyl)benzyl]-2-thioxo-1,2,3,5-tetrahydro-4H-pyrrolo[3,2-d]pyrimidin-4-one;
1-{2-[(methylamino)methyl]-4-(trifluoromethyl)benzyl}-2-thioxo-1,2,3,5-tetrahydro-4H-pyrrolo[3,2-d]pyrimidin-4-one; and
pharmaceutically acceptable salts thereof.

It shall be noted that any one of these specific compounds may be disclaimed from any of the herein mentioned embodiments.

In one embodiment there is provided a process for the preparation of compounds of formula (I) or pharmaceutically acceptable salts of compounds of formula (I), and the intermediates used in the preparation thereof.

Another embodiment is a product obtainable by any of the processes or examples disclosed herein.

Further, because of the fact that the absolute configuration of the enantiomers of the compounds disclosed herein was determined by a spectroscopy study, rather than by for instance an X-ray study (see working Example 3(b)), it is to be understood that the R and S designation will be reversed should the results from said spectroscopic study for one reason or to another be proven wrong.

Medical and Pharmaceutical Use

The compounds of formula (I) and their pharmaceutically acceptable salts are useful because they possess pharmacological activity as inhibitors of the enzyme MPO.

The compounds of formula (I) and their pharmaceutically acceptable salts are indicated for use in the treatment or prophylaxis of diseases or conditions in which modulation of the activity of the enzyme myeloperoxidase (MPO) is desirable. In particular, linkage of MPO activity to disease has been implicated in cardiovascular diseases. Therefore the disclosed compounds are particularly indicated for use in the treatment of coronary artery disease and heart failure conditions or disorders in mammals including man. Further, the disclosed compounds are particularly indicated for use in the treatment of chronic kidney disease (CKD), cardiorenal syndrome (CRS), non-alcoholic steatohepatitis (NASH) and arrhythmia conditions or disorders in mammals including man.

Conditions or disorders that may be specifically mentioned include coronary artery disease, acute coronary syndrome, heart failure, heart failure with reduced ejection fraction and heart failure with preserved ejection fraction.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening or identified through specific biomarker pattern to be particularly susceptible to developing the disease or condition.

For the above-mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect concerns a pharmaceutical composition comprising a novel compound of formula (I), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, *Pharmaceuticals—The Science of Dosage Form Designs*, M. E. Aulton, Churchill Livingstone, $2^{nd}$ Ed. 2002. The pharmaceutical composition preferably comprises less than 80% and more preferably less than 50% of a compound of formula (I), or a pharmaceutically acceptable salt thereof.

In one embodiment there is provided a compound of formula (I), or a pharmaceutically acceptable salt of a compound of formula (I), for use in therapy, especially in the prevention or treatment of cardiovascular disease in a mammal, particularly a human.

In a further embodiment there is provided a compound of formula (I), or a pharmaceutically acceptable salt of a compound of formula (I), for use in therapy, especially in the prevention or treatment of a condition where inhibition of MPO would be beneficial.

In still a further embodiment there is provided a compound of formula (I), or a pharmaceutically acceptable salt of a compound of formula (I), for use in therapy, especially in the prevention or treatment of coronary artery disease in a mammal, particularly a human.

In still a further embodiment there is provided a compound of formula (I), or a pharmaceutically acceptable salt of a compound of formula (I), for use in therapy, especially in the prevention or treatment of acute coronary syndrome in a mammal, particularly a human.

In still a further embodiment there is provided a compound of formula (I), or a pharmaceutically acceptable salt of a compound of formula (I), for use in therapy, especially in the prevention or treatment of heart failure in a mammal, particularly a human.

In still a further embodiment there is provided a compound of formula (I), or a pharmaceutically acceptable salt of a compound of formula (I), for use in therapy, especially in the prevention or treatment of heart failure with reduced ejection fraction in a mammal, particularly a human.

In still a further embodiment there is provided a compound of formula (I), or a pharmaceutically acceptable salt of a compound of formula (I), for use in therapy, especially in the prevention or treatment of heart failure with preserved ejection fraction in a mammal, particularly a human.

In still a further embodiment there is provided a compound of formula (I), or a pharmaceutically acceptable salt of a compound of formula (I), for use in therapy, especially in the prevention or treatment of CKD in a mammal, particularly a human.

In still a further embodiment there is provided a compound of formula (I), or a pharmaceutically acceptable salt of a compound of formula (I), for use in therapy, especially in the prevention or treatment of CRS in a mammal, particularly a human.

In still a further embodiment there is provided a compound of formula (I), or a pharmaceutically acceptable salt of a compound of formula (I), for use in therapy, especially in the prevention or treatment of NASH in a mammal, particularly a human.

In still a further embodiment there is provided a compound of formula (I), or a pharmaceutically acceptable salt of a compound of formula (I), for use in therapy, especially in the prevention or treatment of arrhythmia in a mammal, particularly a human.

In one embodiment there is provided a method of treating, or reducing the risk of, diseases or conditions in which inhibition of the enzyme MPO is beneficial which comprises administering to a person suffering from or at risk of, said disease or condition, a therapeutically effective amount of a compound of formula (I), or a pharmaceutically acceptable salt thereof.

In a further embodiment there is provided a method of treating, or reducing the risk of, cardiovascular disorders, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, coronary artery disease, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, acute coronary syndrome, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, heart failure, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, heart failure with reduced ejection fraction, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, heart failure with preserved ejection fraction, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, CKD, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, CRS, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, NASH, in a person suffering from or at risk of, said disease or condition, wherein the method comprises administering to the person a therapeutically effective amount of a compound of formula (I), or a pharmaceutically acceptable salt thereof.

In still a further embodiment there is provided a method of treating, or reducing the risk of, arrhythmia, in a person suffering from or at risk of, said disease or condition, wherein the method comprises administering to the person a therapeutically effective amount of a compound of formula (I), or a pharmaceutically acceptable salt thereof.

In one embodiment there is provided a pharmaceutical formulation comprising a therapeutically effective amount of a compound of formula (I), or a pharmaceutically acceptable salt of a compound of formula (I), and a pharmaceutically acceptable diluent, excipient and/or inert carrier.

In a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of a condition where inhibition of MPO would be beneficial.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of coronary artery disease in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of acute coronary syndrome in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of heart failure in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of heart failure with reduced ejection fraction in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of heart failure with preserved ejection fraction in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of CKD in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of CRS in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of NASH in a mammal, particularly a human.

In still a further embodiment there is provided a pharmaceutical formulation comprising a compound of formula (I), or a pharmaceutically acceptable salt of a compound of formula (I), in admixture with a pharmaceutically acceptable adjuvant, diluent or carrier, for use in therapy, especially in the prevention or treatment of arrhythmia in a mammal, particularly a human.

There is also provided a process for the preparation of such a pharmaceutical composition which comprises mixing the ingredients.

In one embodiment, plasma urate levels may be used as a stratifying tool and a pharmacodynamic biomarker for MPO inhibitor treatment.

To contextualize MPO into HFpEF pathophysiology, a set of MPO-related biomarkers were quantified in plasma from HFpEF patients, i.e. the KaRen cohort (*Eur. J. Heart Failure*, 2009, 11, 198-204). The cohort represents patients diagnosed with HFpEF that were followed up for events 18 months after inclusion of the study. In addition to ECG and echocardiography data at inclusion, the registry also includes data on medication, medical history and clinical chemistry data. In addition to levels of MPO and the activity thereof, the following biomarkers were quantified (mechanistic rationale/link within parenthesis): calprotectin, lipocalin-2 (NGAL), sTNFR1 (neutrophil/monocyte involvement), arginine (Arg), asymmetric (ADMA) and symmetric (SDMA) dimethyl arginine, endothelin-1 (vascular health); urate and allantoin (purine catabolism and oxidative tone), TIMP-1, TIMP-4 and osteopontin (tissue remodelling).

A supervised principal component analysis—orthogonal projection to latent structures by partial least square analysis (OPLS)—were performed to identify and rank variables (n=256) explaining the symptomatic severity of the disease (NYHA score (The Criteria Committee of the New York Heart Association. Nomenclature and Criteria for the Diagnosis of Diseases of the Heart and Great Vessels. 9th ed. Boston, Mass.: Little, Brown & Co; 1994: 253-256)). The KaRen registry dataset were merged with the MPO-related biomarker data obtained from plasma drawn at study inclusion of the patient. All data were scaled to unit variance and mean centered. In addition, variables with a max/mean-ratio >10, were log-transformed to increase equal leverage of all variables. This generated a data matrix consisting of 257 variables in 86 patients that was subjected to principal component analysis using Simca 13 (Umetrics, Umeå, Sweden). In the OPLS analysis, variables (loadings) contributing to the predicted response, in this case NYHA score, can be separated from loadings varying independently of the response, hence orthogonal variables. The informative variables can in turn be either positively or negatively correlating to the response. The higher the magnitude of the loading value (either positive or negative), the better the correlation to the predicted response. The OPLS model predicting NYHA score explained 50% (R2Y=0.50) of the variation of NYHA score, with a Q2 value of 0.26 after a full Jack knife cross validation as implemented in the SIMCA software.

As indicated by the amplitude of the loading values shown in FIG. 1, the majority of the MPO-related biomarkers were good predictors of the NYHA score, arguing that these biomarkers represent active participation in the pathophysiology, and not merely act as bystanders (as would have been suggested by close-to-zero loading values). Interestingly, all biomarkers but osteopontin, Arg, and ADMA performed better than did NT-proBNP in predicting NYHA score.

The co-clustering of the MPO-related biomarkers with urate and its oxidation product allantoin (also corroborated by significant correlation between urate and all of the individual biomarkers when analyzed in a univariate fashion, Table 1) suggests that urate may in fact be a biomarker for inflammation and tissue hypoxia due to poor vascular function.

We postulate that tissue hypoxia, the degree of which will be determined by the degree of inflammation and vascular function, has impact on plasma urate concentration. Myocardial ischemia results in accelerated loss of ATP and a corresponding buildup of urate levels in rat hearts (*Am. J. Physiol. Heart Circ. Physiol.*, 2004, 286, H677-H684; *J. Biol. Chem.*, 1995, 270, 18797-18803). Furthermore, increased myocardial production of urate contributes to systemic urate levels and correlates to NYHA class in heart failure patients (*Circ. J.*, 2006, 70, 1006-1011).

Figure 2:
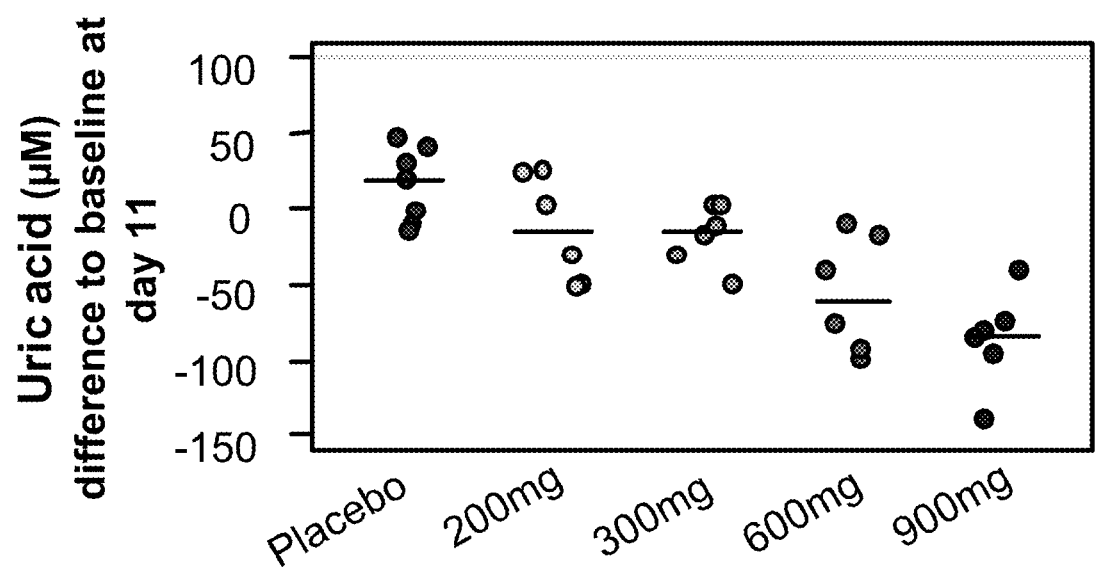
FIG. 2 shows the dose-dependent reduction of uric acid by the MPO-inhibitor AZD3241 in Healthy Volunteers. Subjects received placebo or the indicated daily dose for 10 days, and the difference in plasma urate levels versus baseline was calculated. Each symbol represents one subject.

Myeloperoxidase deposited in the vascular wall (*J. Clin. Invest.*, 2001, 108, 1759-1770) has been shown to drive vascular dysfunction both in healthy (*Eur. Heart J.*, 2012, 33, 1625-1634) and in diseased individuals (*Circulation*, 2004, 110, 1134-1139; *Circulation*, 2006, 113, 1871-1878). We therefore suggest that myeloperoxidase inhibition will result in improved vascular function (as supported by data from MPO-deficient humans, *Eur. Heart J.*, 2012, 33, 1625-1634), which will improve tissue perfusion and oxygen supply and thereby decrease local production and thus systemic concentrations of urate. This hypothesis is also supported by data from clinical trials using two distinct myeloperoxidase inhibitors (AZD5904 (http://open-innovation.astrazeneca.com/what-we-offer/compound/azd5904/?_sm_au_=isH0QK1bJkWQtMf7) and AZD3241 (*Nuclear Medicine and Biology*, 2015, 42, 555-560), both of which dose-dependently reduced urate levels in healthy objects (data shown for AZD3241 in FIG. 2 (ClinicalTrials-.gov Identifier NCT00914303).

Figure 3:
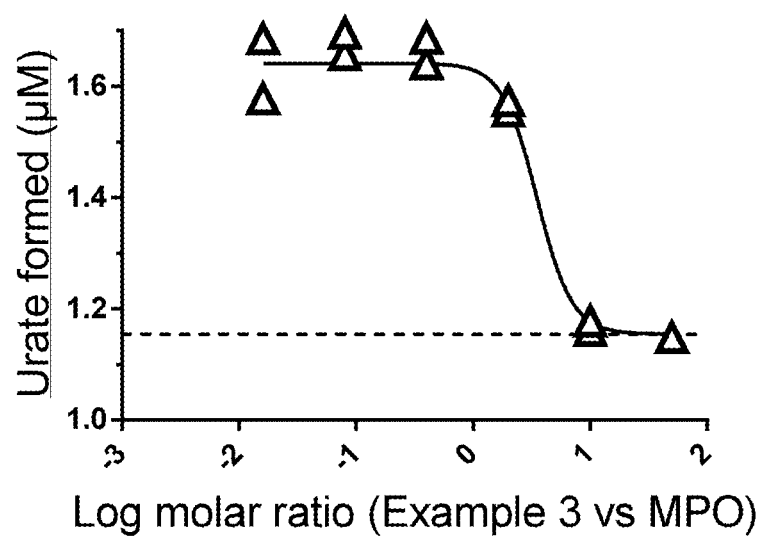
FIG. 3 shows that activated MPO drives the production of urate in vitro. Activated MPO was incubated with xanthine and titrated amounts of Example 3: 1-{2-[(1R)-1-aminoethyl]-4-chlorobenzyl}-2-thioxo-1,2,3,5-tetrahydro-4H-pyrrolo[3,2-d]pyrimidin-4-one for 80 min, after which urate levels were quantified by LC-MS. The dotted line represents the urate formed in the presence of unactivated MPO.

In addition to MPOs role in maintaining elevated urate levels due to poor perfusion as discussed above, we also propose that MPO per se may generate urate by oxidizing xanthine in concert with xanthine oxidase. This occurs when activated MPO encounters xanthine in vitro, and the increased urate production can be concentration-dependently inhibited by Example 3 (FIG. 3).

In a further embodiment, plasma urate level may be used as a stratifying tool and a pharmacodynamic biomarker for MPO inhibitor treatment in combination with other biomarkers or clinical characteristics to identify patients with poor vascular function (and thus high inflammatory tone according to OPLS analysis above).

In still a further embodiment, there is provided a method of identifying patients suitable for MPO inhibitor treatment encompassing the measurement of plasma urate levels.

The compounds of formula (I) herein exemplified, when tested in an MPO binding assay, for example Test A described below, preferably with an $IC_{50}$ less than 50 µM. The compounds of formula (I) also display a promising pharmacological profiles by separating desired and undesired effects in vivo.

These and other embodiments are described in greater detail herein below, where further aspects will be apparent to one skilled in the art from reading this specification.

Pharmacological Properties

The compounds of formula (I) or pharmaceutically acceptable salts thereof are believed to be useful in the prevention or treatment of cardiovascular conditions, including but not limited to coronary artery disease, acute coronary syndrome, heart failure, heart failure with reduced ejection fraction and heart failure with preserved ejection fraction in a mammal, particularly a human.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

Combination Therapy

The compounds of formula (I), or a pharmaceutically acceptable salt thereof, may also be administered in conjunction with other compounds used for the treatment of the above conditions.

In another embodiment, there is a combination therapy wherein a compound of formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

Compounds described herein may be of use in treating cardiovascular, metabolic and renal disease in combination with agents that are
  cardiac therapies,
  anti-hypertensives,
  diuretics,
  peripheral vasodilators,
  lipid modifying agents,
  anti-diabetic,
  anti-inflammatory, or
  anti-coagulant.

Examples of the above include, but are not restricted to, digitalis glycosides, anti-arrhythmics, calcium channel antagonists, ACE inhibitors, angiotensin receptor blockers (e.g. Valsartan), endothelin receptor blockers, β-blockers, thiazide diuretics, loop diuretics, cholesterol synthesis inhibitors such as statins (e.g. Rosuvastatin), cholesterol absorption inhibitors, cholesterylester transfer protein (CETP) inhibitors, anti-diabetic drugs such as insulin and analogues, GLP-1 analogues, sulphonamides, dipeptidyl peptidase 4 inhibitors, thiazolidinediones, SGLT-2 inhibitors, and anti-inflammatory drugs such as NSAID's and CCR2 antagonists, anti-coagulants such as heparins, thrombin inhibitors and inhibitors of factor Xa, platelet aggregation inhibitors, P2X7 antagonists and neprilysin inhibitors (e.g. Sacubitril).

When used in a combination therapy, it is contemplated that the compounds of formula (I) or pharmaceutically acceptable salts thereof and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where inhibition of MPO is required, which method comprises administration of a therapeutically effective amount of a compound of formula (I) to a person suffering from, or susceptible to, such a condition.

The compounds of formula (I) will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical formulations are described in, for example, *Pharmaceuticals—The Science of Dosage Form Designs*, M. E. Aulton, Churchill Livingstone, 2$^{nd}$ Ed. 2002.

Suitable daily doses of the compounds of formula (I) in therapeutical treatment of humans are about 0.0001-100 mg/kg body weight, preferably 0.01-10 mg/kg body weight.

Oral formulations are preferred, particularly tablets or capsules which may be formulated by methods known to those skilled in the art to provide doses of the active compound in the range of 0.007 mg to 700 mg for example 1 mg, 3 mg, 5 mg, 10 mg, 25 mg, 50 mg, 100 mg and 250 mg.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

According to a further aspect there is thus provided a pharmaceutical formulation comprising a compound of formula (I), or pharmaceutically acceptable derivatives thereof, in admixture with a pharmaceutically acceptable adjuvant, diluent and/or carrier.

The compounds of formula (I) may be present in the pharmaceutical formulation in a concentration from 0.1 to 99.5%, such as from 0.5 to 95%, by weight of the total formulation.

Preparation of the Compounds

In another aspect there is provided a process for preparing a compound of the formula (I), or a pharmaceutically acceptable salt thereof, which process comprises:

a) reacting a compound of the formula (II) with a compound of the formula (III):

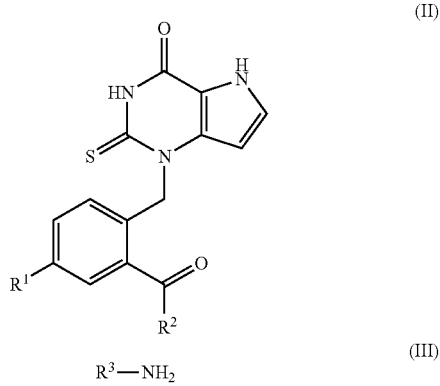

wherein $R^1$, $R^2$ and $R^3$ are as defined in formula (I) and the conditions are such that a reductive alkylation of the compounds of the formula (III) forms an N—C bond between the nitrogen atom of the compounds of formula (III) and the carbon atom of the aldehyde group, or ketone group, of the compounds of formula (II), and where necessary converting the resultant compound of formula (I) into a pharmaceutically acceptable salt thereof, and where desired separating the resultant compound of formula (I) into its individual optical isomers; or b) reacting a compound of the formula (II), wherein $R^1$ and $R^2$ are as defined in formula (I), with hydroxylamine or a salt thereof whereupon the formed oxime intermediate is treated with a reducing agent and the conditions are such that a single bond is formed between the nitrogen atom of the hydroxylamine compound and the carbon atom of the aldehyde group, or ketone group, of the compounds of formula (II) and simultaneously the hydroxyl group, which is attached to the nitrogen atom, is replaced by a hydrogen atom, and the obtained primary amine derivative optionally is converted into a secondary amine compound in order to introduce substituent $R^3$, which is defined in formula (I), by a conventional reductive alkylation process using an appropriate aldehyde or ketone compound and a reducing agent, and where necessary converting the resultant compound of formula (I) into a pharmaceutically acceptable salt thereof, and where desired separating the resultant compound of formula (I) into its individual optical isomers; or c) treating a compound of the formula (IV) with a deprotection reagent:

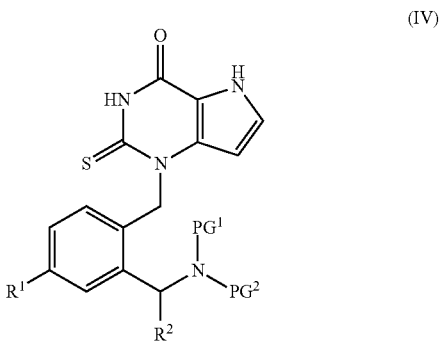

wherein R¹ and R² are as defined in formula (I) and PG¹ and PG² are protecting groups, which may be the same as each other, and the obtained primary amine derivative optionally is converted into a secondary amine compound in order to introduce substituent R³, which is defined in formula (I), by a conventional reductive alkylation process using an appropriate aldehyde or ketone compound and a reducing agent, and where necessary converting the resultant compound of formula (I) into a pharmaceutically acceptable salt thereof, and where desired separating the resultant compound of formula (I) into its individual optical isomers.

The compounds of formula (II) and (III) are reacted with each other under conditions of reductive alkylation. The reaction is typically performed at a non-extreme temperature, for example 0-40° C., in a substantially inert solvent for example N-methylpyrrolidone. The reaction mixture may also be heated by microwave irradiation at a higher temperature, for instance above 100° C. Typical reducing agents include borohydrides such as sodium cyanoborohydride. The reduction reaction may also be metal-catalysed by the use of such as, for instance, tetraisopropoxytitanium.

The compounds of formula (II) and the hydroxylamine compound are reacted with each other under conditions of oxime formation followed by reduction. The reaction is typically performed at a non-extreme temperature, for example 20-70° C., in a substantially inert solvent for example HOAc. Typical reducing agents include metals such as zinc.

The compounds of formula (IV) are reacted with a deprotection reagent under conventional conditions for removing protecting groups. Typically, the protecting groups are two tert-butyloxycarbonyl groups and typical deprotection agents include acids such as hydrogen chloride. The reaction is typically performed at a temperature of about 30-50° C., in an organic solvent, e.g. MeOH.

The compounds of the formula (II) may be prepared, for example by reacting a compound of formula (V) with benzoyl isothiocyanate:

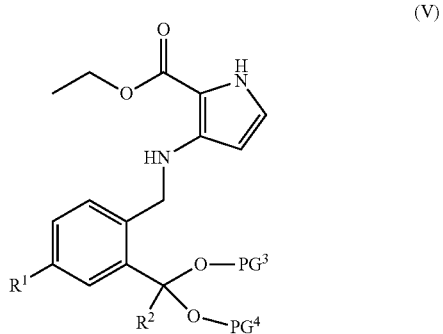

(V)

wherein R¹ and R² are as defined in formula (I) and PG³ and PG⁴ are protecting groups, which may or may not be the same as each other, and, which may or may not be connected to each other to form a ring. The reaction conditions are such that a six membered 2-thiopyrimidinone ring is formed, and finally the resultant intermediate is treated with a deprotection reagent in order to remove the protecting groups PG³ and PG⁴ to give a compound of formula (II).

The compounds of the formula (III) are commercially available, known in the art or may be prepared in conventional manner known by the person skilled in the art.

The compounds of the formula (IV) may be prepared, e.g. by reacting a compound of formula (VI) with benzoyl isothiocyanate:

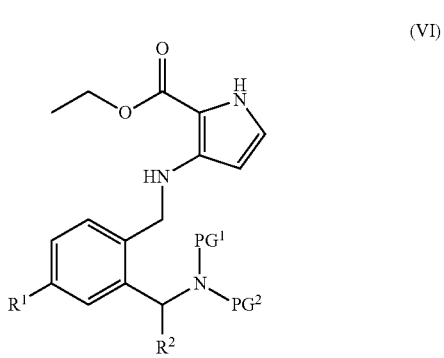

(VI)

wherein R¹ and R² are as defined in formula (I) and PG¹ and PG² are as defined in formula (IV) and the reaction conditions are such that a six membered 2-thiopyrimidinone ring is formed to give a compound of formula (IV).

In the cyclization reactions as hereinbefore set forth a compound of formula (V), or a compound of formula (VI), and the benzoyl isothiocyanate are slowly added to each other in a suitable organic solvent, such as MeOH, and stirred until reaction is complete, typically at room temperature for between 5 min to 4 h, and if necessary, overnight. Typically a base, such as $Cs_2CO_3$, is then added and the mixture may be stirred at an elevated temperature for a prolonged time such as, for instance, at 60° C. for 3-4 h. After reaction is complete, the mixture is usually treated with an acid, such as HOAc, to give the required compound of formula (II) or of formula (IV).

The compounds of the formula (V) may be prepared, for example by reacting ethyl 3-amino-1H-pyrrole-2-carboxylate with a compound of formula (VII):

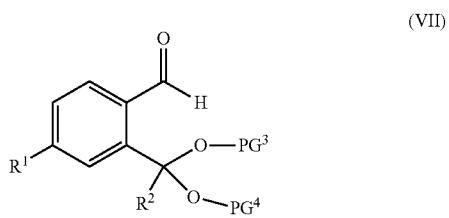

(VII)

wherein R¹ and R² are as defined in formula (I) and PG³ and PG⁴ are as defined in formula (V) and the reaction conditions are conventional reductive alkylation conditions. Usually, the amine compound, as a hydrochloride salt, is treated with N,N-diisopropylethylamine and HOAc in an organic solvent e.g. ethanol, and then the aldehyde compound of formula (VII) is added. After the mixture has been stirred for some time, e.g. at room temperature for 1 h, the reducing agent, such as sodium cyanoborohydride, is added and the resultant mixture is stirred until the reaction is complete, e.g. at room temperature for 1-20 h, to give the compound of formula (V).

The compounds of the formula (VI) may be prepared, for example by reacting under reductive alkylation conditions ethyl 3-amino-1H-pyrrole-2-carboxylate with a compound of formula (VIII):

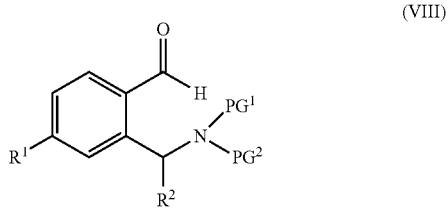

wherein $R^1$ and $R^2$ are as defined in formula (I) and $PG^1$ and $PG^2$ are as defined in formula (IV). Usually, the amine compound is introduced as a hydrochloride salt, which then is treated with an excess of N,N-diisopropylethylamine before the aldehyde compound is added. Preferably, the reducing agent, such as sodium cyanoborohydride, is added after the mixture of the amino compound and the aldehyde compound has been stirred at room temperature for a prolonged time such as e.g. for 18 h. The reaction is typically carried out in an alcohol as solvent, such as MeOH or ethanol, at room temperature and in the presence of HOAc.

The compounds of the formula (VII) may be prepared as shown in Scheme 1 below and by methods analogous to those described in the examples.

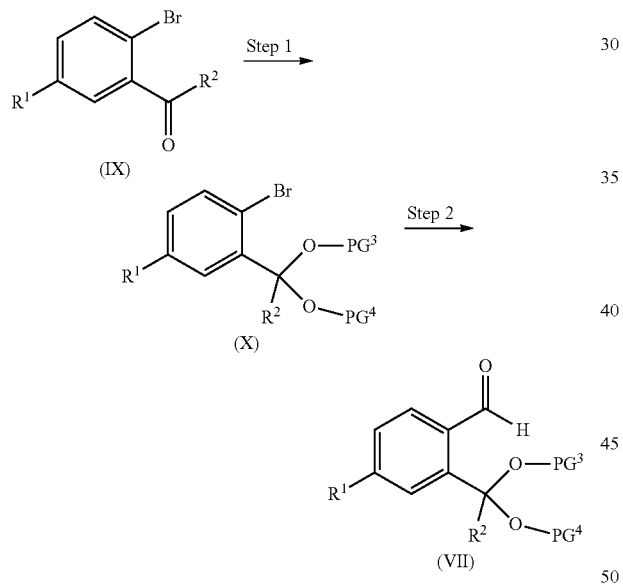

DMF. The reaction is preferably carried out at a low temperature such as e.g. at −78° C.

The compounds of the formula (VIII) may be prepared as shown in Scheme 2 below and by methods analogous to those described in the examples.

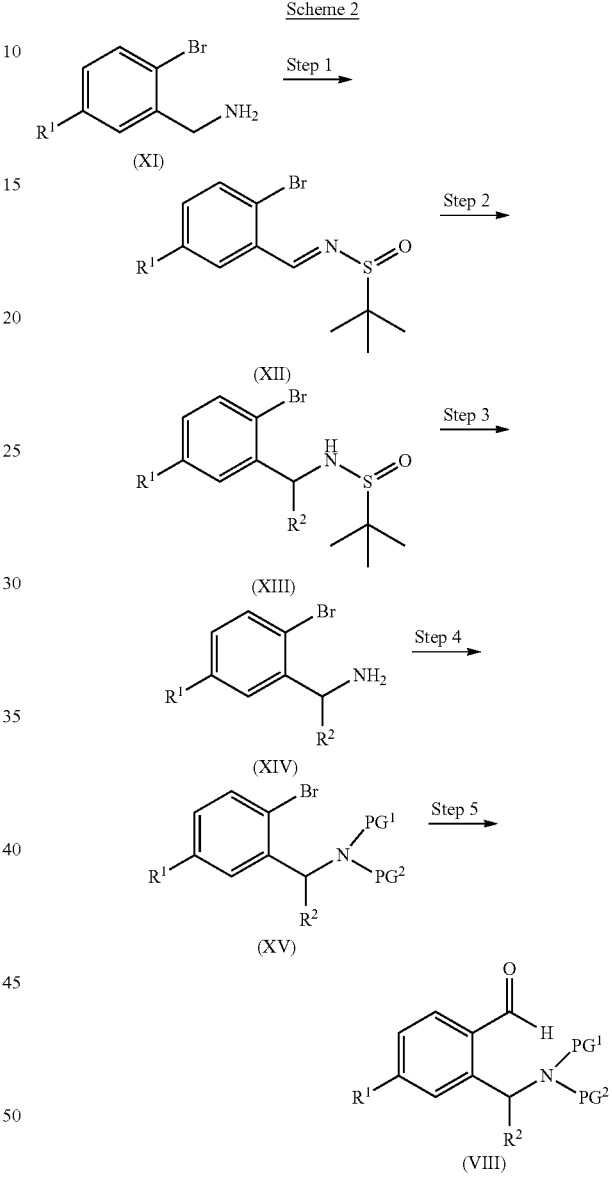

Step 1: A compound in accordance with formula (X), wherein $R^1$, $R^2$, $PG^3$ and $PG^4$ are as previously defined, can be obtained by reacting a compound with formula (IX) in which $R^1$ and $R^2$ are as previously defined with an appropriate alcohol or diol, such as e.g. ethane-1,2-diol in the presence of an acid, such as e.g. 4-methylbenzenesulfonic acid, in an appropriate solvent, such as e.g. toluene. The compounds of the formula (IX), wherein $R^1$ and $R^2$ are as previously defined, are known in the art or may be prepared in a conventional manner known by the skilled chemist.

Step 2: A compound in accordance with formula (VII), wherein $R^1$, $R^2$, $PG^3$ and $PG^4$ are as previously defined, can be obtained by treating a compound with formula (X) in which $R^1$, $R^2$, $PG^3$ and $PG^4$ are as previously defined, with a strong base, such as e.g. butyllithium in an inert solvent, such as e.g. THF, and then treating the resultant mixture with Step 1: A compound in accordance with formula (XII) can be obtained by reacting a compound with formula (XI), wherein $R^1$ is as previously defined, with one of the enantiomers of 2-methylpropane-2-sulfinamide in the presence of a base, such as e.g. cesium carbonate in an organic solvent, such as e.g. dichloromethane. The compounds of the formula (XI), are known or may be prepared in a conventional manner known by the skilled chemist.

Step 2: A compound in accordance with formula (XIII), wherein $R^1$ and $R^2$ are as previously defined, can be obtained by reacting a compound with formula (XII) with a Grignard reagent, such as e.g. $R^2MgBr$, wherein $R^2$ is as previously defined, in an inert solvent, such as e.g. dichloromethane, and optionally separating the obtained intermediate into its diastereomers by conventional methods, such as e.g. by silica gel chromatography.

Step 3: A compound in accordance with formula (XIV), wherein $R^1$ and $R^2$ are as previously defined, can be obtained by treating a compound with formula (XIII) with a deprotection reagent, such as e.g. hydrogen chloride in an organic solvent, such as e.g. MeOH. Typically, the acid is added while cooling and then the resultant solution is stirred until reaction is complete e.g. at room temperature for 1-3 h.

Step 4: A compound in accordance with formula (XV), wherein $R^1$, $R^2$, $PG^1$ and $PG^2$ are as previously defined, can be obtained by treating a compound with formula (XIV) with appropriate reagents for sequentially introducing the suitable protecting groups $PG^1$ and $PG^2$. Typically, the amine compound is successively treated with two portions of di-tert-butyl dicarbonate in the presence of N,N-dimethylpyridin-4-amine. The reaction is typically performed in an organic solvent, such as e.g. dichloromethane or 2-methyltetrahydrofurane, at a temperature of from about room temperature to about 80° C.

Step 5: A compound in accordance with formula (VIII), wherein $R^1$, $R^2$, $PG^1$ and $PG^2$ are as previously defined, can be obtained by treating a compound with formula (XV) with synthesis gas in the presence of a catalyst, which may such as e.g. be a mixture of diacetoxypalladium, di((3S,5S,7S)-adamantan-1-yl)(butyl)-phosphine and tetramethylethylenediamine, in an organic solvent, such as for instance toluene. Typically, the reaction is performed at about 5 bar and at about 100° C. for about 21 h. Alternatively, a compound with formula (XV) is treated with carbon monoxide in the presence of dichlorobis (p-dimethylamino phenyldit-butylphosphine) palladium (II), triethylsilane and a base, such as for instance N,N-diisopropylethylamine. That reaction is typically performed in DMSO as a solvent and it is usually carried out at an elevated temperature and at an increased pressure for a prolonged time, such as e.g. at a temperature of, or above, 90° C., at a pressure of about 4-5 bar and for 24 h.

The protection and deprotection of functional groups is described in *Protective Groups in Organic Synthesis*, 4$^{th}$ Ed, T. W. Greene and P. G. M. Wuts, Wiley-Interscience (2006) and *Protecting Groups*, 3$^{rd}$ Ed, P. J. Kocienski, Georg Thieme Verlag (2005).

A further embodiment encompasses pharmaceutically acceptable salts of the compounds of formula (I).

A salt of a compound of formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts.

For reviews on suitable salts, see Berge et al., *J. Pharm. Sci.*, 1977, 66, 1-19 or *Handbook of Pharmaceutical Salts: Properties, selection and use*, P. H. Stahl, P. G. Vermuth, IUPAC, Wiley-VCH, 2002.

Where an acid co-former is a solid at r.t. and there is no or only partial proton transfer between the compound of formula (I) and such an acid co-former, a co-crystal of the co-former and compound of formula (I) may result rather than a salt. All such co-crystal forms of the compound of formula (I) are encompassed herein.

It is also to be understood that certain compounds of formula (I) may exist in solvated form, e.g. hydrates, including solvates of a pharmaceutically acceptable salt of a compound of formula (I).

In a further embodiment, certain compounds of formula (I) may exist as racemates and racemic mixtures, single enantiomers, individual diastereomers and diastereomeric mixtures. Certain compounds of formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In a further embodiment, the compounds of formula (I) encompass any isotopically-labelled (or "radio-labelled") derivatives of a compound of formula (I). Such a derivative is a derivative of a compound of formula (I) wherein one or more atoms are replaced by an atom having an atomic mass or mass number different from the atomic mass or mass number typically found in nature. Examples of isotopes that may be incorporated include $^2H$ (also written as "D" for deuterium).

In a further embodiment, the compounds of formula (I) may be administered in the form of a prodrug which is broken down in the human or animal body to give a compound of the formula (I).

Various forms of prodrugs are known in the art. For examples of prodrug derivatives, see: *Nature Reviews Drug Discovery* 2008, 7, 255 and references cited therein.

Intermediate compounds may also exist in enantiomeric forms and may be used as purified enantiomers, diastereomers, racemates or mixtures.

Pharmacological Activity

Methods for the determination of MPO inhibitory activity are disclosed in WO 02/090575. The pharmacological activity of compounds disclosed herein was tested in the following screen (Test A) in which the compounds were tested in the presence of ascorbate, which reacts with MPO-derived hypochlorous acid (HOCl) to form dehydro-ascorbate. The loss of ascorbate is followed by measuring absorbance at 260 nm.

Assay buffer: 100 µM diethyl triamine pentaacetic acid (DTPA) in buffer consisting of 10 mM $Na_2HPO_4/NaH_2PO_4$, 3 mM KCl in 140 mM NaCl, pH 7.4.

Enzyme solution: MPO purified from the human cell line HL60, 1.38 nM (final concentration 0.7 nM) and L-ascorbate, 100 µM (final concentration 50 µM) in Assay buffer Substrate solution: $H_2O_2$, 98 µM (final concentration 49 µM)

Forty µL of the enzyme solution was added to 0.6 µL compound serially diluted in DMSO. Absorbance was measured at 260 nm to obtain a compound blank value. After an additional 10 min, 40 µL of the substrate solution was added and the absorbance at 260 nm was recorded between 4 and 40 min to obtain kinetic readings of enzyme activity. IC50 values of the compounds tested were obtained using recordings of absorbance at 260 nm 20 minutes after substrate addition and calculated using standard procedures.

To detect thyroid peroxidase (TPO) inhibitory activity, the production of hypoiodous acid (HOI) was quantified. HOI was detected by reacting it with methionine, which is converted to dehydro-methionine, which in turn is detected by reacting it with excess iodide at acidic pH. The reaction converts $I^-$ to $I_3^-$ that has absorbance at 353 nm. In brief, 0.6 µL compound serially diluted in DMSO was added to 25 µL 50 nM baculovirus-expressed recombinant human TPO (obtained from RSR Ltd, Cardiff, UK) in assay buffer (100 mM $Na_2HPO_4/NaH_2PO_4$, pH 7.4), after which absorbance at 353 nm was read to obtain a blank value. The enzyme reaction was initiated by the addition of 25 µL of a mix consisting of 2 mM methionine, 20 µM NaI and 100 µM $H_2O_2$ in assay buffer, and stopped by the addition of 10 µL catalase, 0.25 mg/mL. After an additional 5 min, 25 µL 600 mM sulphuric acid followed by 25 µL 100 mM KI were added, and absorbance at 353 nm was read 5 min after this addition. $IC_{50}$ values of the compounds tested were obtained using standard procedures.

In general, the compounds disclosed herein, which were tested, had a surprisingly high selectivity for the MPO enzyme over the TPO enzyme within the range of 220-1600 for the ratio $IC_{50}$ (TPO)/$IC_{50}$ (MPO). The majority of the compounds (80%) demonstrated a corresponding ratio of the $IC_{50}$ values of said enzymes that was higher than 500. On the other hand, prior art compounds according to WO 2006/062465, which were tested, demonstrated a corresponding ratio within the range of 1-92 and the majority of those compounds (92%) had a ratio that was less than 50. Accordingly, the compounds disclosed herein approximately showed a ten times higher MPO/TPO selectivity as compared to the selectivity of the prior art compounds according to WO 2006/062465.

The $IC_{50}$ values (MPO and TPO) for the Example compounds are set forth in Table 2 herein below. Also, the ratio TPO to MPO, which demonstrates the selectivity for MPO over TPO, for each Example compound, is given in Table 2.

TABLE 2

| Ex. No. | Inhibition of MPO $IC_{50}$ (µM) | Inhibition of TPO $IC_{50}$ (µM) | $IC_{50}$ (TPO)/ $IC_{50}$ (MPO) |
|---|---|---|---|
| 1 | 0.0086 | 4.4 | 512 |
| 2 | 0.007 | 8.8 | 1257 |
| 3 | 0.007 | 4.3 | 614 |
| 4b | 0.042 | 68 | 1620 |
| 5 | 0.019 | 8.9 | 468 |
| 6 | 0.022 | 10 | 455 |
| 7 | 0.015 | 11 | 710 |
| 8 | 0.013 | 13 | 952 |
| 9 | 0.029 | 16 | 552 |
| 10 | 0.01 | 11 | 1100 |
| 11 | 0.014 | 19 | 1357 |
| 12 | 0.054 | 46 | 852 |
| 13 | 0.024 | 38 | 1609 |
| 14 | 0.04 | 28 | 697 |
| 15 | 0.049 | 11 | 224 |

EXAMPLES

The following examples are non-limiting examples. The following abbreviations are employed herein:
APCI atmospheric pressure chemical ionization
aq aqueous
$Cs_2CO_3$ cesium carbonate
$CH_2Cl_2$ dichloromethane
DIPEA N,N-diisopropylethylamine
DMAP N,N-dimethylpyridin-4-amine
DMF N,N-dimethylformamide
DMSO dimethyl sulfoxide
$Et_2O$ diethyl ether
EtOAc ethyl acetate
EtOH ethanol
FA formic acid
h hour(s)
HOAc acetic acid
HPLC high performance liquid chromatography
HCl hydrogen chloride
$KHSO_4$ potassium hydrogensulfate
$K_2CO_3$ potassium carbonate
MeCN acetonitrile
MeOH methanol
$MgSO_4$ magnesium sulfate
min minutes
MS mass spectrum
$Na_2SO_4$ sodium sulfate
$NaHCO_3$ sodium bicarbonate
NMP N-methylpyrrolidone
$NH_3$ ammonia
$NH_4OAc$ ammonium acetate
NMR nuclear magnetic resonance
r.t. room temperature
sat. saturated
TEA triethylamine
TFA trifluoroacetic acid
THF tetrahydrofuran
TMEDA tetramethylethylenediamine The following general experimental procedures were used:
(i) Phase Separators used in the experimental are ISOLUTE® Phase Separator columns.
(ii) Straight Phase flash chromatography was performed using SP1™ Purification system from Biotage™ using normal phase silica FLASH+™ (40M, 25M or 12M) or SNAP™ KP-Sil Cartridges (340, 100, 50 or 10).
(iii) Purification by preparative reverse-phase HPLC was performed using a Kromasil® prep C8 10 µM 250×50 mm column typically using a gradient of MeCN in water/MeCN/HOAc 95/5/0.2 as mobile phase, or a SunFire™ Prep C18 5 µM OBD 19×150 mm column using a gradient of MeCN in water/MeCN/FA 95/5/0.2 as mobile phase, or using a gradient of MCCN in water/MeCN/0.1 µM $NH_4OAc$ as mobile phase.
(iv) $^1H$ NMR measurements were performed on Varian INOVA 400, 500 and 600 spectrometers or Bruker Avance 400, 500 and 600 spectrometers operating at $^1H$ frequencies of 400, 500 and 600 MHz, respectively. The experiments were typically recorded at 25° C.
(v) In general, all solvents used were analytical grade and commercially available anhydrous solvents were routinely used for reactions.

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York.

X-ray powder diffraction data was measured with Corundum as an internal reference. The X-ray powder diffraction (referred to herein as XRPD) pattern was determined by mounting a sample on a zero background holder, single silicon crystal, and spreading out the sample into a thin layer.

The powder X-ray diffraction was recorded with a Theta-Theta PANalytical X'Pert PRO (wavelength of X-rays 1.5418 Å nickel-filtered Cu radiation, Voltage 45 kV, filament emission 40 mA). Automatic variable divergence and anitscatter slits were used and the samples were rotated during measurement. Samples were scanned from 2-50° 2-theta using a 0.013° step width and a 44.37 s count time, together with a PIXEL detector (active length 3.35° 2-theta).

The X-ray powder diffraction (XRPD) pattern was obtained in Bragg-Brentano geometry. It is known that an X-ray powder diffraction pattern may be obtained which has one or more measurement errors depending on measurement conditions, such as equipment or machine used (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures). Persons skilled in the art of X-ray powder diffraction will realize that the relative intensity of peaks can be affected by, for example, grains above 30 microns in size and non-unitary aspect ratios that may affect analysis of samples. Furthermore, it should be understood that intensities might fluctuate depending on experimental conditions and sample preparation (e.g. preferred orientation). The following definitions have been used for the relative intensity (%): 25-100%, vs (very strong); 10-25%, s (strong); 3-10%, m (medium); 1-3%, w (weak).

The skilled person will also realize that the position of reflections can be affected by the precise height at which the sample sits in the diffractometer and the zero calibration of the diffractometer. The surface planarity of the sample may also have a small effect. Hence the diffraction pattern data presented are not to be taken as absolute values. Generally, a measurement error of a diffraction angle in an X-ray powder diffractogram may be approximately plus or minus 0.2° 2-theta, and such a degree of a measurement error should be taken into account when considering the X-ray powder diffraction data.

Chemical IUPAC names are generated by software ACD/Labs 2012 provided by Advanced Chemistry Development, Inc. Toronto, Ontario, Canada MSC 1B5.

Example 1

1-{2-[(1R)-1-Aminopropyl]-4-chlorobenzyl}-2-thioxo-1,2,3,5-tetrahydro-4H-pyrrolo[3,2-d]pyrimidin-4-one

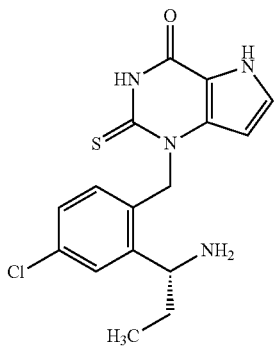 [SMILES: CC[C@@H](N)c1cc(Cl)ccc1Cn1c(=S)[nH]c(=O)c2[nH]ccc21]

(a) tert-Butyl [(1R)-1-(2-bromo-5-chlorophenyl)propyl]carbamate

To a solution of (R)-1-(2-bromo-5-chlorophenyl)propan-1-amine hydrochloride (obtained in a similar way as the intermediate (R)-1-(2-bromo-5-chlorophenyl)ethanamine was obtained in Example 3(c) but using ethylmagnesium bromide rather than methylmagnesium bromide) (0.97 g, 3.40 mmol) in $CH_2Cl_2$ (15 mL) was added TEA (1.42 mL, 10.21 mmol) and di-tert-butyl dicarbonate (0.82 g, 3.74 mmol). The mixture was stirred at r.t. overnight and then washed with an aq solution of $KHSO_4$. The aq phase was extracted with $CH_2Cl_2$ (20 mL) and the combined organic solutions were concentrated in vacuo. The residue was purified on a silica gel column using a mixture of heptane and EtOAc (gradient, 0 to 15% EtOAc) as eluent, obtaining 1.42 g (quantitative yield) of the title compound as a white solid. MS (APCI+) m/z 349 $[M+H]^+$.

(b) di-tert-butyl [(1R)-1-(2-bromo-5-chlorophenyl)propyl]imidodicarbonate

To a solution of tert-butyl [(1R)-1-(2-bromo-5-chlorophenyl)propyl]carbamate (1.19 g, 3.40 mmol) in 2-methyltetrahydrofuran (32 mL) were added di-tert-butyl dicarbonate (1.49 g, 6.81 mmol) and DMAP (0.83 g, 6.81 mmol). The mixture was stirred at 50° C. and then di-tert-butyl dicarbonate (0.75 g, 3.40 mmol) and another portion of DMAP (0.42 g, 3.40 mmol) were added. After another 4 h of stirring at 50° C., still another portion of di-tert-butyl dicarbonate (0.37 g, 1.70 mmol) was added and the mixture was stirred at 50° C. overnight. More of di-tert-butyl dicarbonate (0.75 g, 3.40 mmol) and DMAP (0.42 g, 3.40 mmol) were added and stirring was continued for 30 min. The mixture was washed with an aq solution of $KHSO_4$ (M), dried trough a phase separator and then evaporated. The crude product was purified on a silica gel column using a mixture comprising heptane and EtOAc as eluent (gradient, 0 to 12% EtOAc). There was obtained 1.10 g (72%) of the title compound as colourless oil. $^1H$ NMR (400 MHz, DMSO-$d_6$): δ 0.93 (t, 3H), 1.37 (d, 18H), 1.8-2.19 (m, 2H), 5.17 (dd, 1H), 7.33 (dd, 1H), 7.57 (d, 1H), 7.65 (d, 1H).

(c) Di-tert-butyl [(1R)-1-(5-chloro-2-formylphenyl)phenyl)propyl]imidodicarbonate A mixture of di-tert-butyl [(1R)-1-(2-bromo-5-chlorophenyl)]-imidodicarbonate (1.05 g, 2.34 mmol), diacetoxypalladium (0.053 g, 0.23 mmol), di((3S,5S,7S)-adamantan-1-yl)(butyl)phosphine (0.26 g, 0.70 mmol) and TMEDA (0.26 mL, 1.75 mmol) was dissolved in toluene (4 mL) and the resultant solution was sealed in an autoclave. The autoclave was filled with synthesis gas (carbon monoxide/hydrogen, 1:1) at 5 bar and then heated in an oil-bath for 21 h at 100° C. The crude product was purified by silica gel chromatography using a gradient of heptane and EtOAc as eluent (0 to 18% EtOAc) to yield 0.53 g (57%) of the title compound. $^1H$ NMR (400 MHz, DMSO-$d_6$): δ 0.95 (t, 3H), 1.35 (s, 18H), 1.85-2.02 (m, 1H), 2.03-2.19 (m, 1H), 5.90 (dd, 1H), 7.60 (dd, 1H), 7.69 (d, 1H), 7.87 (d, 1H), 10.22 (s, 1H).

(d) Ethyl 3-[(2-{(1R)-1-[bis(tert-butoxycarbonyl)amino]propyl}-4-chlorobenzyl)amino]-1H-pyrrole-2-carboxylate To a mixture of ethyl 3-amino-H-pyrrole-2-carboxylate hydrochloride (0.29 g, 1.53 mmol) and EtOH (99.5%, 4 mL) were added DIPEA (0.46 mL, 2.66 mmol) and di-tert-butyl [(1R)-1-(5-chloro-2-formylphenyl)propyl]-imidodicarbonate (0.53 g, 1.33 mmol) dissolved in EtOH (99.5%, 2.5 mL). The mixture was stirred at r.t. overnight. HOAc (0.23 mL, 4.00 mmol) was added and the mixture was stirred at r.t. for 2.5 h whereupon sodium cyanotrihydroborate (0.088 g, 1.40 mmol) was added portion-wise during a period of 3 min. The reaction mixture was then stirred at r.t. for 45 min and then diluted with water. After extracting twice with EtOAc, the organic solutions were combined and then washed twice with an aq solution of citric acid (0.5 M), twice with an aq solution of bicarbonate and finally with brine (half saturated). The solution was dried over MgSO$_4$ and the solvent was removed by evaporation to give 0.68 g (95%) of the title compound. $^1$H NMR (400 MHz, DMSO-d$_6$): δ 0.91 (t, 3H), 1.27 (t, 3H), 1.32 (s, 18H), 1.98-2.05 (m, 1H), 2.09-2.23 (m, 1H), 4.16-4.28 (m, 3H), 4.41 (dd, 1H), 5.26-5.33 (m, 1H), 5.43 (s, 1H), 5.82 (bs, 1H), 6.68 (t, 1H), 7.32 (s, 2H), 7.42 (s, 1H), 10.77 (s, 1H).

(e) Di-tert-butyl [(1R)-1-{5-chloro-2-[(4-oxo-2-thioxo-2,3,4,5-tetrahydro-1H-pyrrolo[3,2-d]pyrimidin-1-yl)methyl]phenyl}propyl]imidodicarbonate Benzoyl isothiocyanate (0.20 mL, 1.51 mmol) was added dropwise to a solution of ethyl 3-[(2-{(1R)-1-[bis(tert-butoxycarbonyl)amino]propyl}-4-chlorobenzyl)amino]-1H-pyrrole-2-carboxylate (0.68 g, 1.26 mmol) in MeOH (4 mL) was added. The mixture was stirred at r.t. for 3 h and then Cs$_2$CO$_3$ (0.86 g, 2.64 mmol) was added. The mixture was heated at 65° C. for 2 h and then cooled to 10° C. HOAc (0.32 mL, 5.67 mmol) was slowly added followed by a slow addition of water (8 mL). The mixture was extracted with EtOAc and the organic solution was dried (Na$_2$SO$_4$). The solvent was removed by evaporation and there was obtained 0.94 g (quantitative yield) of the title compound.

To the crude mixture of di-tert-butyl [(1R)-1-{5-chloro-2-[(4-oxo-2-thioxo-2,3,4,5-tetrahydro-1H-pyrrolo[3,2-d]pyrimidin-1-yl)methyl]phenyl}propyl]imidodicarbonate (0.69 g, 1.26 mmol) was added HCl (1.25 M in MeOH, 7.05 mL, 8.81 mmol). The mixture was stirred at 50° C. for 1 h and then cooled to 10° C. Water (2 mL) and then an aq solution of NH$_3$ (25%, 0.63 mL, 8.81 mmol) was slowly added to adjust the pH to 9.2. The formed precipitate was collected by filtration and washed with a mixture of water and MeOH (2:1, 2 mL). There was obtained 0.15 g (34.6%) of the title compound with an enantiomeric excess of 98.8%. $^1$H NMR (400 MHz, DMSO-d$_6$): δ 0.91 (t, 3H), 1.52-1.72 (m, 2H), 4.08 (t, 1H), 5.73 (dd, 2H), 6.03 (d, 1H), 6.59 (d, 1H), 7.11 (dd, 1H), 7.30 (d, 1H), 7.58 (d, 1H). [α]$_D^{20}$=+37.2° (c=0.5, EtOH). MS (APCI+) m/z 349 [M+H]$^+$.

Example 2

1-[2-(1-Aminoethyl)-4-chlorobenzyl]-2-thioxo-1,2,3,5-tetrahydro-4H-pyrrolo[3,2-d]pyrimidin-4-one

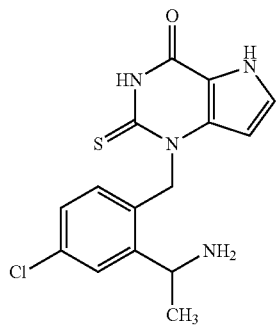 [SMILES: CC(N)c1cc(Cl)ccc1Cn1c(=S)[nH]c(=O)c2[nH]ccc21]

(a) 2-(2-Bromo-5-chlorophenyl)-2-methyl-1,3-dioxolane 1-(2-Bromo-5-chlorophenyl)ethanone (8.29 g, 35.50 mmol) was dissolved in toluene (180 mL) in a round-bottomed flask fitted with a Dean-Stark trap. Ethane-1,2-diol (5.% mL, 106.51 mmol) and 4-methylbenzenesulfonic acid (0.67 g, 3.91 mmol) were added and the reaction mixture was heated at reflux for 3.5 h. The reaction mixture was cooled to r.t., an aq solution of K$_2$CO$_3$ (1 M) was added and the layers were separated. The aq phase was extracted with toluene and the combined organic layers were washed with water and with brine. The solution was dried (MgSO$_4$), filtered and the solvent was removed under reduced pressure to give 9.29 g (94%) of the title compound. $^1$H NMR (500 MHz, CDCl$_3$): δ 1.80 (s, 3H), 3.78 (m, 2H), 4.08 (m, 2H), 7.13 (m, 1H), 7.52 (m, 1H), 7.66 (m, 1H).

(b) 4-Chloro-2-(2-methyl-1,3-dioxolan-2-yl)benzaldehyde

Under a nitrogen atmosphere and at −78° C., butyllithium (2.5 M in hexane, 14.73 mL, 36.82 mmol) was added dropwise to a solution of 2-(2-bromo-5-chlorophenyl)-2-methyl-1,3-dioxolane (9.29 g, 33.47 mmol) in THF (100 mL) during 30 min and the resulting solution was stirred at −78° C. for 30 min. DMF (3.87 mL, 50.21 mmol) was added dropwise at −78° C. After the addition was complete, the reaction was allowed to warm to r.t. and stirring was continued for 10 min. The reaction mixture was quenched with an aq solution of NH$_4$Cl (sat.) and the phases were separated. The aq phase was extracted twice with EtOAc. The combined organic layers were washed with brine, dried (MgSO$_4$) and the solvents were removed under reduced pressure. The product was purified by flash chromatography (silica gel, elution with a gradient of EtOAc and heptane 10% to 20%) to give 5.95 (78%) of the title compound as transparent colourless oil. $^1$H NMR (500 MHz, CDCl$_3$): δ 1.68 (s, 3H), 3.64-3.66 (m, 2H), 3.94-3.97 (m, 2H), 7.24-7.28 (m, 1H), 7.52-7.54 (m, 1H), 7.74-7.77 (m, 1H), 10.52-10.53 (m, 1H).

(c) Ethyl 3-{[4-chloro-2-(2-methyl-1,3-dioxolan-2-yl)benzyl]amino}-1H-pyrrole-2-carboxylate Ethyl 3-amino-1H-pyrrole-2-carboxylate hydrochloride (3.65 g, 19.17 mmol) was dissolved in EtOH (99.5%, 100 mL) and to the solution were added DIPEA (3.34 mL, 19.17 mmol) followed by HOAc (1.99 mL, 34.85 mmol). The reaction mixture was cooled to 10° C. and then 4-chloro-2-(2-methyl-1,3-dioxolan-2-yl)benzaldehyde (3.95 g, 17.43 mmol) dissolved in EtOH (99.5%, 10 mL) was added. The reaction mixture was allowed to reach r.t. for 1 h. Sodium cyanotrihydroborate (1.31 g, 20.91 mmol) was added and the mixture was stirred at r.t. for 18 h. The reaction mixture was quenched with water (50 mL) and the pH was adjusted to ~11 with NaOH. The mixture was extracted trice with EtOAc. The combined organic layers were washed with brine, dried (MgSO$_4$) and the solvent was removed under reduced pressure. The product was purified by flash chromatography (isocratic, heptane/EtOAc, 90/10) to give 4.61 g (72%) of the title compound as a colourless gum. $^1$H NMR (400 MHz, CDCl$_3$): δ 1.3-1.37 (m, 3H), 1.71 (s, 3H), 3.79-3.85 (m, 2H), 4.05-4.1 (m, 2H), 4.25-4.35 (m, 2H), 4.51-4.57 (m, 2H), 5.64-5.71 (m, 1H), 6.66-6.73 (m, 1H), 7.2-7.24 (m, 1H), 7.4-7.45 (m, 1H), 7.57-7.6 (m, 1H).

(d) 1-[4-Chloro-2-(2-methyl-1,3-dioxolan-2-yl)benzyl]-2-thioxo-1,2,3,5-tetrahydro-4H-pyrrolo[3,2-d]pyrimidin-4-one Benzoyl isothiocyanate (1.70 mL, 12.64 mmol) was added dropwise to a solution of ethyl 3-{[4-chloro-2-(2-methyl-1,3-dioxolan-2-yl)benzyl]amino}-1H-pyrrole-2-carboxylate (4.61 g, 12.64 mmol) in MeOH (14 mL) and the reaction mixture was stirred at r.t. for 10 min. A further portion of benzoyl isothiocyanate (0.17 mL, 1.26 mmol) was added and the reaction was stirred for 30 min. Cs$_2$CO$_3$ (8.85 g, 27.17 mmol) was added and the mixture was stirred at 60° C. for 1.5 h. The solvent was removed under reduced pressure. Water (30 mL) and EtOAc (70 mL) were added and a precipitate being formed in the organic phase was isolated by filtration. After washing the solid with Et$_2$O, there was obtained 4.71 g (99%) of the title compound as a white solid. $^1$H NMR (600 MHz, DMSO-d$_6$): δ 1.75 (s, 3H), 3.78-3.83 (m, 2H), 4.05-4.11 (m, 2H), 5.63-5.67 (m, 1H), 6.56-6.63 (m, 1H), 6.93-6.98 (m, 1H), 7.17-7.22 (m, 1H), 7.45-7.5 (m, 1H). MS (APCI−) m/z 376 [M−H]$^-$.

(e) 1-(2-Acetyl-4-chlorobenzyl)-2-thioxo-1,2,3,5-tetrahydro-4H-pyrrolo[3,2-d]pyrimidin-4-one To a suspension of 1-[4-chloro-2-(2-methyl-1,3-dioxolan-2-yl)benzyl]-2-thioxo-1,2,3,5-tetrahydro-4H-pyrrolo[3,2-d]pyrimidin-4-one (4.71 g, 12.47 mmol) in CH$_2$Cl$_2$ (25 mL) was added TFA (9.26 mL, 124.65 mmol). The reaction mixture was stirred at r.t. for 2 h and then an aq solution of NaOH (3.8 M) was added until a pH of approximately 11 was reached. The formed solid was isolated by filtration and the product was washed with CH$_2$Cl$_2$ and then with Et$_2$O. There was obtained 3.49 g (84%) of the title compound as a white solid. $^1$H NMR (600 MHz, DMSO-d$_6$): δ 2.69 (s, 3H), 5.63-5.7 (m, 1H), 5.79-5.83 (m, 2H), 6.79-6.86 (m, 1H), 6.89-6.95 (m, 1H), 7.4-7.5 (m, 1H), 7.96-8.04 (m, 1H). MS (APCI−) m/z 332 [M−H]$^-$.

(f) 1-[2-(1-Aminoethyl)-4-chlorobenzyl]-2-thioxo-1,2,3,5-tetrahydro-4H-pyrrolo[3,2-d]pyrimidin-4-one To a mixture of 1-(2-acetyl-4-chlorobenzyl)-2-thioxo-1,2,3,5-tetrahydro-4H-pyrrolo[3,2-d]pyrimidin-4-one (3.39 g, 10.16 mmol), HOAc (20 mL) and NMP (40 mL) was added hydroxylamine hydrochloride (0.78 g, 11.18 mmol) and the mixture was then stirred at 60° C. for 18 h. Zinc (1.02 g, 15.59 mmol) was added and the reaction mixture was stirred at 60° C. for 4 h. A further portion of zinc (1 g, 15.30 mmol) was added and the mixture was then stirred at 60° C. for additional 4 h. Another portion of zinc (1 g, 15.30 mmol) was added and after additional 20 h stirring at 80° C. still another portion of zinc (3 g, 45.89 mmol) was added. The mixture was then stirred at 80° C. for 40 h and the remaining solids were filtered off. The product was purified by preparative HPLC (3 injections) on a C8 column using a gradient of 0-70% MeCN in a mixture of water/MeCN/HOAc (95/5/0.2) over 15 min (the elution started with 0% MCCN for 5 min). There was obtained 0.86 g (25%) of the title compound. $^1$H NMR (600 MHz, DMSO-d$_6$, 40° C.): δ 1.33-1.37 (m, 3H), 4.38-4.45 (m, 1H), 5.64-5.85 (m, 2H), 6.01-6.05 (m, 1H), 6.59-6.64 (m, 1H), 7.1-7.15 (m, 1H), 7.27-7.31 (m, 1H), 7.64-7.66 (m, 1H). MS (APCI−) m/z 333 [M−H]$^-$.

Example 3

1-{2-[(1R)-1-Aminoethyl]-4-chlorobenzyl}-2-thioxo-1,2,3,5-tetrahydro-4H-pyrrolo[3,2-d]pyrimidin-4-one

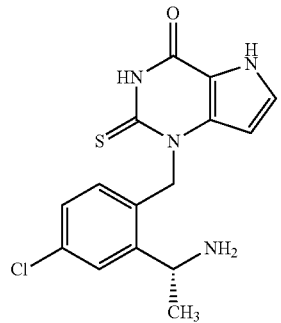 [SMILES: C[C@@H](N)c1cc(Cl)ccc1Cn1c(=S)[nH]c(=O)c2[nH]ccc21]

(a) S-(E or Z)-N-(2-Bromo-5-chlorobenzylidene)-2-methylpropane-2-sulfinamide S-(E or Z)-N-(2-Bromo-5-chlorobenzylidene)-2-methylpropane-2-sulfinamide (5.41 g, 16.78 mmol) was dissolved in CH$_2$Cl$_2$ (200 mL) under a nitrogen atmosphere and to the resultant solution was added methylmagnesium bromide (11.18 mL, 33.55 mmol) at −45° C. The mixture was stirred between −40° C. and −50° C. for 4 h and was then slowly allowed to reach r.t. over night. A solution of NH$_4$Cl (sat., 50 mL) was added followed by water (100 mL). The layers were separated using a phase separator and the aqueous layer was extracted three times with CH$_2$Cl$_2$ (150 mL). The combined organic layers were concentrated in vacuo. The residue was purified by silica gel chromatography using a mixture comprising heptane and EtOAc (gradient, 10% to 60% EtOAc). The fractions containing the major diastereomer—which eluted last from the column—were pooled and the solvent removed by evaporation. There was obtained 5.28 g (93%) of the title compound. $^1$H NMR (400 MHz, DMSO-d$_6$): δ 1.15 (s, 9H), 1.30 (d, 3H), 4.65 (m, 1H), 6.10 (d, 1H), 7.30 (d, 1H), 7.65 (d, 1H), 7.70 (s, 1H). MS (APCI+) m/z 340 [M+H]$^+$.

The absolute configuration of the title compound was determined by vibrational circular dichroism (VCD) spectroscopy using a material that was obtained from a similar experiment as in Example 3(b). Based on results from comparing the obtained experimental spectrum with simulated spectra of the two possible diastereomers using density functional theory calculations, there was a clear agreement between the experimental spectrum and the simulated spectrum of the diastereomer having R-configuration at the asymmetric carbon atom.

(c) (R)-1-(2-Bromo-5-chlorophenyl)ethanamine (S)—N-[(1R)-1-(2-Bromo-5-chlorophenyl)ethyl]-2-methylpropane-2-sulfinamide (5.25 g, 15.50 mmol) was treated with a MeOH solution of HCl (1.25 M, 150 mL, 187.50 mmol) at r.t. for 1.5 h. The solvent was removed by evaporation. The remainder was dissolved in CH$_2$Cl$_2$ (200 mL) and the solution washed with aq NaHCO$_3$ (100 mL). The aq phase was extracted with CH$_2$Cl$_2$ (200 mL) and the combined organic layers were concentrated in vacuo, to give 4.02 g (quantitative yield) of the title compound, which was used in the next step without further purification. $^1$H NMR (400 MHz, CDCl$_3$): δ 1.40 (d, 3H), 4.40 (q, 1H), 7.10 (d, 1H), 7.40 (d, 1H), 7.60 (s, 1H).

(d) tert-Butyl [(1R)-1-(2-bromo-5-chlorophenyl)ethyl]carbamate

To a solution of (R)-1-(2-bromo-5-chlorophenyl)ethanamine (3.64 g, 15.52 mmol) in CH$_2$Cl$_2$ (150 mL) was added TEA (2.58 mL, 18.63 mmol) and di-tert-butyl dicarbonate (3.73 g, 17.07 mmol). The mixture was stirred at room temperature for 3.5 h and then washed with an aq solution of KHSO$_4$ (1 M, 100 mL). The aq phase was extracted with CH$_2$Cl$_2$ (100 mL) and the combined organic solutions were concentrated in vacuo to give 5.83 g (quantitative yield) of the crude title compound. $^1$H NMR (400 MHz, CDCl$_3$): δ 1.25-1.50 (d, 3H), 1.60 (s, 9H), 4.75-5.00 (m, 1H), 7.10 (dd, 1H), 7.30 (m, 1H), 7.50 (d, 1H).

(e) Di-tert-butyl [(1R)-1-(2-bromo-5-chlorophenyl)ethyl]imidodicarbonate

To a solution of tert-butyl [(1R)-1-(2-bromo-5-chlorophenyl)ethyl]carbamate (5.19 g, 15.51 mmol) in 2-methyltetrahydrofuran (150 mL) was added di-tert-butyl dicarbonate (5.08 g, 23.26 mmol) and DMAP (2.84 g, 23.26 mmol). The mixture was stirred at room temperature for 16 h whereupon more di-tert-butyl dicarbonate (1.69 g, 7.75 mmol) and DMAP (0.95 g, 7.75 mmol) were added. The mixture was stirred at 50° C. for 4.5 h and was then concentrated in vacuo. The remainder was dissolved in CH$_2$Cl$_2$ (150 mL) and the solution was washed with KHSO$_4$ (1M, 100 mL) using a phase separator. The aq phase was extracted with CH$_2$Cl$_2$ (100 mL) and the combined organic solutions were concentrated in vacuo. The crude product was purified twice by chromatography on silica gel using a mixture of heptane and EtOAc as eluent (gradient, 30% to 70/of EtOAc). There was obtained 5.05 g (75%) of the title compound. $^1$H NMR (400 MHz, DMSO-d$_6$): δ 1.2-1.4 (m, 21H), 4.70 (m, 1H), 7.25 (dd, 1H), 7.55 (d, 1H), 7.65 (d, 1H).

(f) Di-tert-butyl [(1R)-1-(5-chloro-2-formylphenyl)ethyl]imidodicarbonate

Di-tert-butyl [(1R)-1-(2-bromo-5-chlorophenyl)ethyl] imidodicarbonate (4.27 g, 9.83 mmol), diacetoxypalladium (0.22 g, 0.98 mmol), di((3S,5S,7S)-adamantan-1-yl)(butyl)phosphine (1.06 g, 2.95 mmol) and TMEDA (1.10 mL, 7.37 mmol) were dissolved in toluene (18 mL) and the resultant solution was sealed in an autoclave. The autoclave was filled with synthesis gas (carbon monoxide/hydrogen, 1:1) at 5 bar and then heated in an oil-bath for 21 h at 100° C. The crude product was purified by silica gel chromatography using a gradient of heptane and EtOAc as eluent (0 to 20% EtOAc) to yield 2.15 g (57%) of the title compound. $^1$H NMR (400 MHz, DMSO-d$_6$): δ 1.34 (s, 18H), 1.58 (d, 3H), 6.06 (q, 1H), 7.61 (dd, 1H), 7.67 (d, 1H), 7.87 (d, 1H), 10.14 (s, 1H).

(g) Ethyl 3-[(2-{(1R)-1-[bis(tert-butoxycarbonyl)amino]ethyl}-4-chlorobenzyl)amino]-1H-pyrrole-2-carboxylate To a mixture of ethyl 3-amino-1H-pyrrole-2-carboxylate hydrochloride (1.14 g, 5.99 mmol) and EtOH (99.5%, 20 mL) was added N-ethyl-N-isopropylpropan-2-amine (1.82 mL, 10.42 mmol) followed by di-tert-butyl [(1R)-1-(5-chloro-2-formylphenyl)ethyl]-imidodicarbonate (2.00 g, 5.21 mmol) dissolved in EtOH (99.5%, 5 mL). The mixture was stirred at room temperature overnight. HOAc (0.90 mL, 15.63 mmol) was added and the mixture was stirred at room temperature for 6 h whereupon sodium cyanotrihydroborate (0.34 g, 5.47 mmol) was added portion-wise during a period of 3 min. The reaction mixture was then stirred at room temperature for 1 h and then diluted with water. After extracting with a mixture of EtOAc (25 mL) and toluene (25 mL), the aq solution was extracted with EtOAc (25 mL). The combined organic solutions were washed twice with an aq solution of citric acid (0.5 M, 25 mL), twice with an aq solution of bicarbonate and finally with brine (half sat.). The solution was dried over MgSO$_4$ and then the solvent was removed by evaporation at 40° C. to give 2.93 g (quantitative yield) of the title compound. $^1$H NMR (400 MHz, DMSO-d$_6$): δ 1.27 (t, 3H), 1.31 (s, 18H), 1.59 (d, 1H), 4.21 (m, 3H), 4.37 (dd, 1H), 5.43 (m, 1H), 5.51 (q, 1H), 5.82 (bs, 1H), 6.69 (t, 1H), 7.32 (s, 2H), 7.43 (s, 1H), 10.79 (s, 1H). MS (APCI+) m/z 522 [M+H]$^+$.

(h) Di-tert-butyl [(1R)-1-{5-chloro-2-[4-oxo-2-thioxo-2,3,4,5-tetrahydro-1H-pyrrolo[3,2-d]pyrimidin-1-yl)methyl]phenyl}ethyl]imidodicarbonate To a solution of ethyl 3-[(2-{(1R)-1-[bis(tert-butoxycarbonyl)amino]ethyl}-4-chlorobenzyl)amino]-1H-pyrrole-2-carboxylate (2.79 g, 4.01 mmol) in MeOH (12 mL) was added benzoyl isothiocyanate (0.79 g, 4.81 mmol) dropwise. The mixture was stirred at rt overnight and then Cs$_2$CO$_3$ (2.74 g, 8.42 mmol) was added. The mixture was heated at 60° C. for 3 h and then cooled to 10° C. HOAc (1.03 mL, 18.05 mmol) was added slowly followed by a slow addition of water (24 mL). The formed precipitate was collected by filtration and then washed with MeOH to give 2.09 g (97%) of the title compound as beige solid. $^1$H NMR (400 MHz, DMSO-d$_6$): δ 1.33 (s, 18H), 1.67 (d, 3H), 5.48-5.7 (m, 3H), 5.91 (d, 1H), 6.67 (d, 1H), 7.25 (dd, 1H), 7.32 (d, 1H), 7.48 (d, 1H), 12.43 (s, 2H). MS (APCI+) m/z 533 [M–H]$^-$.

(i) 1-{2-[(1R)-1-Aminoethyl]-4-chlorobenzyl}-2-thioxo-1,2,3,5-tetrahydro-4H-pyrrolo-[3,2-d]pyrimidin-4-one To a crude mixture of di-tert-butyl [(1R)-1-{5-chloro-2-[(4-oxo-2-thioxo-2,3,4,5-tetrahydro-1H-pyrrolo[3,2-d]pyrimidin-1-yl)methyl]phenyl}ethyl]imidodicarbonate (1.67 g, 1.74 mmol) was added HCl (1.25 M, 24.37 mL, 30.46 mmol). The mixture was stirred at 50° C. for 1 h and then cooled with an ice-bath. Water (3 mL) was added and an aq solution of NH$_3$ (25%) was added slowly to pH 9.3. The formed precipitate was collected by filtration to obtain 0.39 g (67%) of the title compound as a beige solid with an enantiomeric excess of 99.9%. $^1$H NMR (400 MHz, DMSO-d$_6$): δ 1.32 (d, 3H), 4.36 (m, 1H), 5.74 (dd, 1H), 6.04 (d, 1H), 6.59 (d, 1H), 7.11 (dd, 1H), 7.31 (d, 1H), 7.65 (d, 1H). [α]$_D^{20}$=+76.8° (c=0.3, MeOH). MS (APCI+) m/z 335 [M+H]$^+$.

(j) 1-{2-[(1R)-1-Aminoethyl]-4-chlorobenzyl}-2-thioxo-1,2,3,5-tetrahydro-4H-pyrrolo[3,2-d]pyrimidin-4-one (Example 3j, prepared as described above) (690 g, 2.06 mol), ethanol (11040 mL) and water (2760 mL) was added to a 50 L vessel under nitrogen. The mobile and free moving slurry was heated to 70° C. for 2.5 h. The reaction was cooled to rt after stirring at 70° C. for 2.5 h. The mixture was filtered (took approximately 2 h to filter) and then washed with 20% water/ethanol (690 mL/2760 mL). The solid was then dried in the oven under vacuum at 50° C. for 3 days to give 633 g (91% yield). ¹H NMR indicated a purity of >95%. ¹H NMR assay indicated a purity of 101%+/−2%, LC indicated a purity of 99.7%, Karl Fischer titration indicated 0.86% water, Pd content indicated 3 ppm and chiral purity indicated 99.9% ep.

Figure 4:
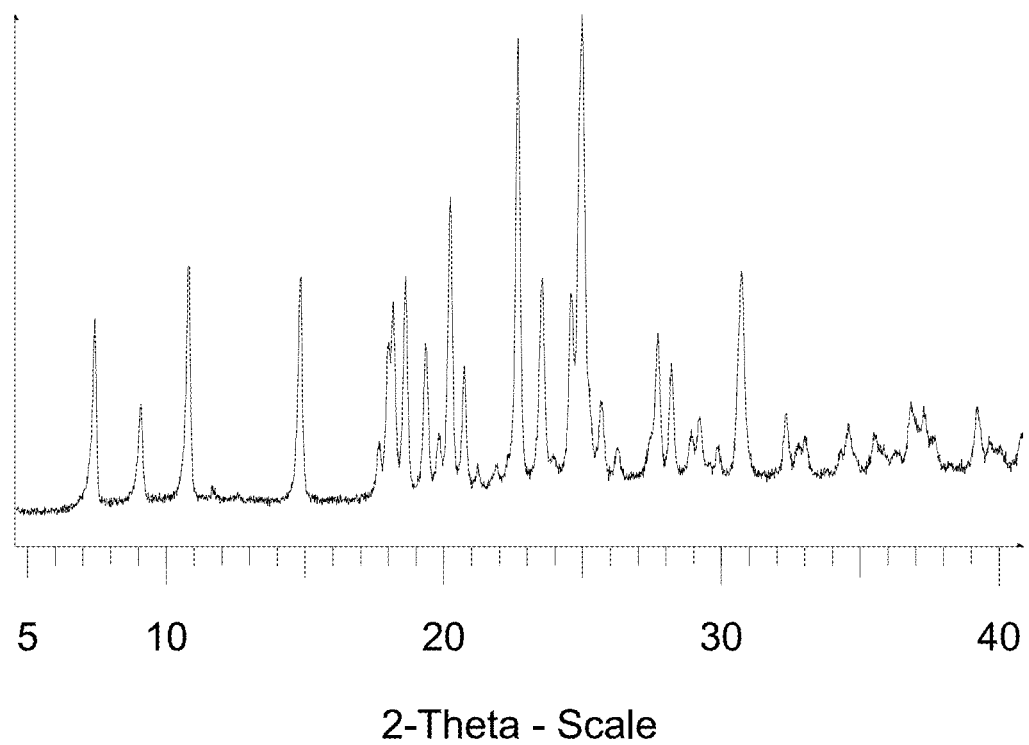
FIG. 4 shows the X-ray powder diffraction pattern for Example 3(j): 1-{2-[(1R)-1-aminoethyl]-4-chlorobenzyl}-2-thioxo-1,2,3,5-tetrahydro-4H-pyrrolo[3,2-d]pyrimidin-4-one.

The solid residue was found to be crystalline by XRPD and a typical diffractogram is displayed in FIG. 4. Characteristic peak positions are listed below.

XRPD pattern 2-Theta (°) 7.4 (vs), 9.0 (s), 10.8 (vs), 14.8 (vs), 20.2 (vs), 22.7 (vs), 23.5 (vs), 25.0 (vs), 30.7 (vs).

The absolute configuration of the title compound was confirmed by single crystal X-ray analysis of the mesylate salt of Example 3.

Example 3, Alternative Preparation

1-{2-[(1R)-1-Aminoethyl]-4-chlorobenzyl}-2-thioxo-1,2,3,5-tetrahydro-4H-pyrrolo[3,2-d]pyrimidin-4-one

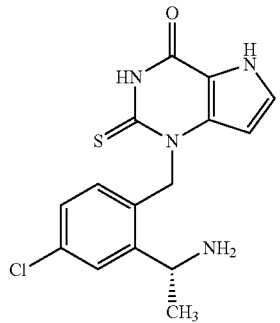

(a) 1-{2-[(1R)-1-Aminoethyl]-4-chlorobenzyl}-2-thioxo-1,2,3,5-tetrahydro-4H-pyrrolo[3,2-d]pyrimidin-4-one A suspension of cesium carbonate (148.5 g, 0.46 mol), 2-bromo-5-chlorobenzaldehyde (100.0 g, 0.46 mmol) and (S)-2-methylpropane-2-sulfinamide (55.1 g, 0.46 mol) in toluene (600 mL) was stirred for 2 h at 40±5° C. then cooled to 30±5° C. The mixture was filtered and the cake washed with toluene (200 mL). The filtrates were combined and concentrated under vacuum. Heptane (1 L) was added and the mixture concentrated under vacuum. This was repeated until the content of toluene was no more than 15.0%. The solution was cooled to 15±5° C. and stirred for 1 h. The mixture was filtered and the cake washed with heptane. The solid was dried under vacuum to give the title compound (141.0 g, 95.2%).

(b) (S)—N-[(1R)-1-(2-Bromo-5-chlorophenyl)ethyl]-2-methylpropane-2-sulfinamide

To a solution of S-(E or Z)-N-(2-bromo-5-chlorobenzylidene)-2-methylpropane-2-sulfinamide (100.0 g, 0.31 mol) in DCM (1.5 L) at 0±5° C. was charged MeMgBr (2.8 M in 2-MeTHF, 0.34 mmol) over 12 h. After an additional 14 h aqueous ammonium chloride (20 wt %, 2 L) was added at 0±10° C. The organic layer was washed twice with saturated NaCl solution (500 mL) and concentrated under vacuum. Heptane (500 mL) was charged and the mixture concentrated under vacuum. This was repeated until the content of both DCM and 2-MeTHF was no more than 5.0%. Petroleum ether 60-90° C. (800 mL) was added and the contents heated to 70-80° C. then cooled to 31-35° C. The mixture was filtered and washed with petroleum ether 60-90° C. (100 mL). After drying under vacuum at 40° C. there was obtained 74.0 g, (70.5%) of the title compound.

(c) tert-Butyl [(1R)-1-(2-bromo-5-chlorophenyl)ethyl]carbamate

To (S)—N-[(1R)-1-(2-Bromo-5-chlorophenyl)ethyl]-2-methylpropane-2-sulfinamide (720 g, 2.1 mol) and 2-MeTHF (3.6 L) was added concentrated HCl (574.0 mL, 6.8 mol) over 1 h at 25±5° C. The solution was stirred for 2 h then aqueous NaOH (15 wt %, 1.8 L) added until a pH of 9 was reached. BOC₂O (485.3 g, 2.2 mol) was added at 20±10° C. and the mixture stirred for 4 h. The mixture was separated and the organic layer washed with aqueous NaOH (4 wt %, 2.0 L) then with aqueous NaCl (20 wt %, 2.0 L), twice. The organic was concentrated under vacuum and heptane (3.6 L) added. The mixture was concentrated again. This process was repeated until the 2-MeTHF content was no more than 5.0%. The solution was cooled to 10±5° C. The mixture was filtered and washed with heptane. After drying under vacuum at 40° C. there was obtained 645.0 g (90.7%) of the title compound.

(d) Di-tert-butyl [(1R)-1-(2-bromo-5-chlorophenyl)ethyl]imidodicarbonate tert-Butyl [(1R)-1-(2-bromo-5-chlorophenyl)ethyl]carbamate (640 g 1.913 mol), DMAP (350.1 g, 2.870 mol) and 2-MeTHF (3.8 L) was heated to 75-80° C. BOC₂O (542.1 g, 2.487 mol) was added dropwise. The solution was stirred at 75-80° C. for 4 h then cooled to 25-30° C. The organic layer was washed with aqueous NaOH (4 wt %, 2 L) then twice with aqueous NaCl (20 wt %, 2 L). The organic layer was concentrated under vacuum then EtOH (3.2 L) added. The mixture was concentrated under vacuum. This process was repeated until the 2-MeTHF content was no more than 5.0%. The solution was heated to 40±5° C. and water (1.6 L) was added. The mixture was cooled to 10±5° C. The mixture was filtered and washed with EtOH:water 1:1 (1.9 L). After drying under vacuum there was obtained the title compound, 770.0 g, (92.0%).

(e) Di-tert-butyl [(1R)-1-(5-chloro-2-formylphenyl)ethyl]imidodicarbonate

A mixture of DMSO (800 mL), N-ethyl-N-isopropylpropan-2-amine (48.1 mL, 276.0 mmol) and triethylsilane (103 mL, 644.0 mmol) was agitated and placed under vacuum (100 mbar) and re-pressurised with nitrogen, three times. The mixture was transferred to a vessel containing di-tert-butyl [(1R)-1-(2-bromo-5-chlorophenyl)ethyl]imidodicarbonate (80.00 g, 184.0 mmol). Bis(di-tert-butyl(4-dimethylaminophenyl)phosphine)dichloropalladium(II) 6.514 g, 9.20 mmol) was added. The contents were pressurised with nitrogen to 2 bar and released back to atmospheric pressure three times, then pressurised with carbon monoxide to 2 bar and released back to atmospheric pressure three times. The vessel was pressurised to 4 bar with carbon monoxide, agitation started and then heated to 90° C. for 24 h. The contents was cooled to 20° C. and filtered. The lower layer was removed and added to a mixture of heptane (400 mL) and water (400 mL). The upper layer was retained and the lower layer was extracted with heptane (200 mL). The lower layer was removed. The two upper layers were combined and washed with water (400 mL) then concentrated to an oil containing the title compound, (66.5 g, 94.0%).

(f) 1-{2-[(1R)-1-Aminoethyl]-4-chlorobenzyl}-2-thioxo-1,2,3,5-tetrahydro-4H-pyrrolo[3,2-d]pyrimidin-4-one To a slurry of di-tert-butyl [(1R)-1-{5-chloro-2-[(4-oxo-2-thioxo-2,3,4,5-tetrahydro-1H-pyrrolo[3,2-d]pyrimidin-1-yl)methyl]phenyl}ethyl]imidodicarbonate (30.0 g, 52.1 mmol) in methanol (200 mL) at 40-45° C. was added 4.0 M HCl in methanol (79.2 mL, 316.8 mmol). The mixture was stirred at 40-45° C. for 1 h then cooled to 20-25° C. Water (96.5 mL) was added. The solution was cooled to 0-10° C. and ammonium hydroxide (56.6%, 31.5 mL, 448 mmol) added to pH 8.5-10. The slurry was filtered and washed with methanol (60 mL) then water (60 mL) then methanol (60 mL). After drying at 70° C. under vacuum there was obtained 16.14 g (92.2%) of the title compound.

Example 4a

1-{2-[(1S)-1-Aminoethyl]-4-chlorobenzyl}-2-thioxo-1,2,3,5-tetrahydro-4H-pyrrolo[3,2-d]pyrimidin-4-one

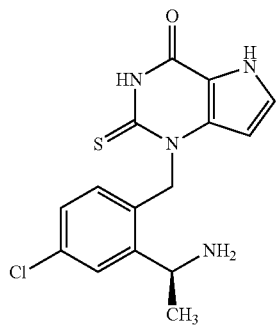 [SMILES: C[C@H](N)c1cc(Cl)ccc1Cn1c(=S)[nH]c(=O)c2[nH]ccc21]

The two enantiomers of 1-[2-(1-aminoethyl)-4-chlorobenzyl]-2-thioxo-1,2,3,5-tetrahydro-4H-pyrrolo[3,2-d]pyrimidin-4-one (Example 2) were obtained by chiral chromatography by using a Chiralpak® IA column (250×4.6 mm, 5 μm) using a mobile phase comprising heptane, EtOH and TEA (80/20/0.1). Starting with 0.66 g of the racemic compound according to Example 2, 0.28 g of the title compound with an enantiomeric excess of 84% was obtained. $[\alpha]_D^{20}$=−14.9° (c=0.5, MeOH).

Example 4b

1-{2-[(1S)-1-Aminoethyl]-4-chlorobenzyl}-2-thioxo-1,2,3,5-tetrahydro-4H-pyrrolo[3,2-d]pyrimidin-4-one

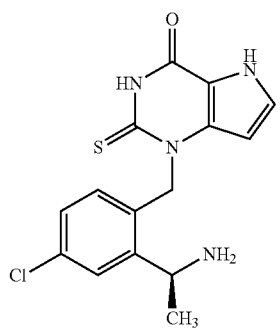 [SMILES: C[C@H](N)c1cc(Cl)ccc1Cn1c(=S)[nH]c(=O)c2[nH]ccc21]

Starting with 2.0 g of 2-bromo-5-chlorobenzaldehyde and using a similar protocol as described in Example 3 but employing the R-enantiomer of 2-methylpropane-2-sulfinamide rather than the S-enantiomer afforded 0.40 g of the title compound with an enantiomeric excess of 99.2%. ¹H NMR (400 MHz, DMSO-d₆) δ 1.34 (d, 3H), 1.91 (s, 3H), 4.41 (q, 1H), 5.57-5.87 (m, 2H), 6.04 (d, 1H), 6.60 (d, 1H), 7.13 (dd, 1H), 7.31 (d, 1H), 7.66 (d, 1H). $[\alpha]_D^{20}$=−43.9° (c=0.5, McOH).

Example 5

1-{4-Chloro-2-[1-(methylamino)ethyl]benzyl}-2-thioxo-1,2,3,5-tetrahydro-4H-pyrrolo[3,2-d]pyrimidin-4-one

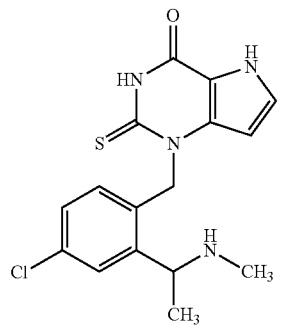 [SMILES: CNC(C)c1cc(Cl)ccc1Cn1c(=S)[nH]c(=O)c2[nH]ccc21]

1-(2-Acetyl-4-chlorobenzyl)-2-thioxo-1,2,3,5-tetrahydro-4H-pyrrolo[3,2-d]pyrimidin-4-one (0.29 g, 0.88 mmol) was suspended in EtOH (99.5%, 2.0 mL) and to the mixture were added tetraisopropoxytitanium (0.52 mL, 1.79 mmol) and methanamine (2 M in THF, 2.68 mL, 5.36 mmol). The mixture was stirred at r.t. for 4 h and then sodium tetrahydroborate (66.9 mg, 1.77 mmol) was added. After stirring at r.t. for 30 min, water and NH₃ (2 M in MeOH) were added to adjust the pH to 11. The suspension was stirred at r.t. for 30 min and then the precipitate was filtered off and washed with MeOH and EtOAc. The filtrate was removed under reduced pressure and the product was then purified by preparative HPLC on a C18 column using a gradient (0-30% MCCN in water, MeCN and FA, 95/5/0.2) as mobile phase. There was obtained 0.13 g (43%) of the title compound. ¹H NMR (500 MHz, DMSO-d₆): δ1.35 (d, 3H), 2.29 (s, 3H), 4.14 (q, 1H), 5.73 (q, 2H), 6.00 (d, 1H), 6.65 (d, 1H), 7.18 (dd, 1H), 7.32 (d, 1H), 7.60 (d, 1H), 8.17 (s, 1H), 12.50 (s, 1H). MS (APCI+) m/z 349 [M+H]⁺.

Example 6

1-{4-Chloro-2-[(ethylamino)methyl]benzyl}-2-thioxo-1,2,3,5-tetrahydro-4H-pyrrolo[3,2-d]pyrimidin-4-one

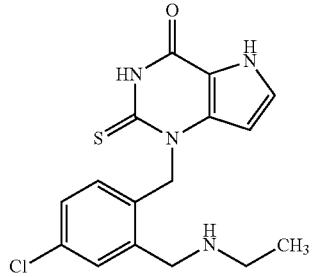 [SMILES: CCNCc1cc(Cl)ccc1Cn1c(=S)[nH]c(=O)c2[nH]ccc21]

(a) 1-Bromo-4-chloro-2-(diethoxymethyl)benzene

A reactor (5 L) was charged with triethyl orthoformate (379 mL, 2278 mmol) under a nitrogen atmosphere and then under stirring, 2-bromo-5-chlorobenzaldehyde (250 g, 1139 mmol) was added in portions during 50 min. The reactor was cooled during the addition to keep the reaction temperature below 21° C. The mixture was stirred at 17° C. for 3 h, another portion of triethyl orthoformate (100 mL, 601 mmol) was added and stirring was then continued for additional 3.5 h. Heptane (300 mL) was added and the mixture was filtered through celite. The filter cake was washed with heptane (200 mL) and the combined solutions were evaporated. The residue was co-evaporated four times with heptane (200 mL) and then purified in portions by silica gel flash chromatography using a mixture comprising EtOAc and hexane as mobile phase (gradient, 0%-50% EtOAc). There was obtained 280 g (84%) of the title compound. $^1$H NMR (400 MHz, DMSO-$d_6$): δ 1.13 (t, 6H), 3.43-3.69 (m, 4H), 5.51 (s, 1H), 7.36 (dd, 1H), 7.48 (d, 1H), 7.63 (d, 1H).

(b) 4-Chloro-2-(diethoxymethyl)benzaldehyde

A reactor (5 L) was charged with 1-bromo-4-chloro-2-(diethoxymethyl)benzene (251 g, 855 mmol) and 2-methyltetrahydrofuran (3 L) under a nitrogen atmosphere and the mixture was cooled to −60° C. To the solution was added n-butyllithium (2.5 M in hexane, 342 mL, 855 mmol) via tubing. After stirring for 40 min, DMF (73 mL, 940 mmol) was added over a period of 12 min. The temperature of the mixture rose to −49° C. during said addition. The mixture was stirred for 40 min and then the temperature was increased to 0° C. After additional 30 min stirring, water (300 mL) was added for a period of 5 min followed by a half sat. solution of brine (1.5 L). The layers were separated and the aq phase was extracted with 2-methyltetrahydrofuran (1 L). The organic solutions were washed with sat. brine, dried (MgSO$_4$) and evaporated overnight at 30° C. There was obtained 193 g of the title compound as light brown oil with a purity of 87% (81% effective yield). $^1$H NMR (400 MHz, CDCl$_3$): δ 1.15 (m, 6H), 3.50-3.70 (m, 4H), 5.90 (s, 1H), 7.40 (dd, 1H), 7.70 (d, 1H), 7.80 (d, 1H).

(c) Ethyl 3-{[4-chloro-2-(diethoxymethyl)benzyl]amino}-1H-pyrrole-2-carboxylate A reactor (10 L) was charged with 4-chloro-2-(diethoxymethyl)benzaldehyde (181 g, 649 mmol) and MeOH (1 L) and to the mixture was added DIPEA (92 g, 714 mmol) dissolved in MeOH (100 mL). Ethyl 3-amino-1H-pyrrole-2-carboxylate hydrochloride (132 g, 648 mmol) was added together with MeOH (700 mL). The mixture was stirred at 20° C. overnight and then HOAc (78 g, 1298 mmol) was added. Sodium cyanoborohydride (4) g, 649 mmol) was added in several portions under a period of 7 min with stirring and cooling, so that the temperature did not rise above 27° C. The solution was stirred for 40 min and then water (1.8 L) was added. The mixture was extracted twice with CH$_2$Cl$_2$ (1 L) and the combined organic solutions were dried (K$_2$CO$_3$) and concentrated to a volume of 1300 mL. After four days the mixture was concentrated in the presence of MeOH to give a MeOH solution (approximately 1 L) of the title compound. The material was used in the next step without further purification. $^1$H NMR (400 MHz, MeOH-$d_4$): δ1.20 (t, 6H), 1.30 (t, 3H), 3.25 (m, 1H), 3.40-3.60 (m, 5H), 4.20 (q, 2H), 4.40 (s, 2H), 5.60 (d, 1H), 5.65 (s, 1H), 6.70 (d, 1H), 7.20 (m, 1H), 7.30 (d, 1H), 7.50 (d, 1H).

(d) 1-[4-Chloro-2-(diethoxymethyl)benzyl]-2-thioxo-1,2,3,5-tetrahydro-4H-pyrrolo[3,2-d]pyrimidin-4-one To a MeOH solution (approximately 1 L) of ethyl 3-{[4-chloro-2-(diethoxymethyl)-benzyl]amino}-1H-pyrrole-2-carboxylate (550 mmol) was slowly added benzoyl isothiocyanate (89 g, 677 mmol) so that the reaction temperature was kept between 17° C. and 22° C. The mixture was stirred for 15 min and another portion of benzoyl isothiocyanate (13.5 g, 82.5 mmol) was added and after additional stirring for 50 min, still another portion of benzoyl isothiocyanate (8 g, 50 mmol) was added. The mixture was stirred for 30 min and then Cs$_2$CO$_3$ (383 g, 1177 mmol) was added during a period of 15 min. The temperature was increased to 30° C. for 30 min and then to 40° C. for 20 min. The mixture stirred at 50° C. for 4 h and then at 10° C. overnight. HOAc (140 mL) was added at 10° C. during a period of 20 min and then the temperature of the mixture was increased to 19° C. To the formed precipitate was slowly added water (1.4 L) and the solid material was isolated by filtration. The filter cake was washed with toluene (2 L) and then dried in vacuo for 3 days. There was obtained 201 g (80%, two steps) of the title compound. $^1$H NMR (600 MHz, DMSO-$d_6$): δ1.20 (m, 6H), 3.50-3.70 (m, 4H), 5.80 (s, 2H), 6.00 (s, 1H), 6.75 (d, 1H), 7.30 (m, 1H), 7.50 (s, 1H), 11.70-12.70 (b, 2H). MS (APCI+) m/z 395 [M+H]$^+$.

(e) 5-Chloro-2-[(4-oxo-2-thioxo-2,3,4,5-tetrahydro-1H-pyrrolo[3,2-d]pyrimidin-1-yl)methyl]benzaldehyde To a cooled mixture of TFA (1.89 mL, 25.39 mmol) and CH$_2$Cl$_2$ (8 mL) was added 1-[4-chloro-2-(diethoxymethyl)benzyl]-2-thioxo-1,2,3,5-tetrahydro-4H-pyrrolo[3,2-d]pyrimidin-4-one (1 g, 2.54 mmol). The ice-bath was removed and the mixture was stirred at r.t. for 2.5 h. The formed precipitate was isolated by filtration and washed with CH$_2$Cl$_2$ to result in 0.69 g (85%) of the title compound as a solid. $^1$H NMR (500 MHz, DMSO-$d_6$): δ 6.02 (s, 2H), 6.09 (s, 1H), 6.88 (d, 1H), 7.31 (t, 1H), 7.60 (dd, 1H), 8.09 (d, 1H), 10.24 (s, 1H), 12.41 (s, 1H), 12.51 (s, 1H). MS (APCI+) m/z 320 [M+H]$^+$.

(f) 1-{4-Chloro-2-[(ethylamino)methyl]benzyl}-2-thioxo-1,2,3,5-tetrahydro-4H-pyrrolo[3,2-d]pyrimidin-4-one 5-Chloro-2-[(4-oxo-2-thioxo-2,3,4,5-tetrahydro-1H-pyrrolo[3,2-d]pyrimidin-1-yl)methyl]benzaldehyde (22 mg, 0.68 mmol) and ethanamine (2 M in THF, 3.39 mL, 6.79 mmol) were dissolved in MeOH (5 mL) in a microwave vial. The reaction mixture was heated by microwave irradiation at 100° C. for 5 min and then at 140° C. for 75 min. Sodium tetrahydroborate (205 mg, 5.43 mmol) was added and the reaction mixture was stirred at r.t. for 3 days. The mixture was quenched by the addition of water. The solvents were evaporated and the crude product was purified by preparative HPLC using a gradient of 0-30% MeCN in water/MeCN/FA (95/5/0.2). $^1$H NMR (600 MHz, DMSO-$d_6$): δ 1.10 (t, 3H), 2.65 (q, 2H), 3.85 (s, 2H), 5.76 (s, 2H), 6.10 (d, 1H), 6.69 (d, 1H), 7.19 (dd, 1H), 7.30 (d, 1H), 7.45 (d, 1H). MS (APCI+) m/z 349 [M+H]$^+$.

Example 7

1-[2-(Aminomethyl)-4-chlorobenzyl]-2-thioxo-1,2,3,5-tetrahydro-4H-pyrrolo[3,2-d]pyrimidin-4-one

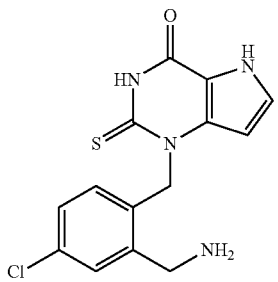 [SMILES: NCc1cc(Cl)ccc1Cn1c(=S)[nH]c(=O)c2[nH]ccc21]

5-Chloro-2-[(4-oxo-2-thioxo-2,3,4,5-tetrahydro-1H-pyrrolo[3,2-d]pyrimidin-1-yl)methyl]benzaldehyde (see Example 6(e)) (194 mg, 0.61 mmol) was added to a mixture of hydroxylamine hydrochloride (46 mg, 0.67 mmol) and HOAc (8°%, 4 mL). The mixture was stirred at r.t. for 5 h and then zinc (198 mg, 3.03 mmol) was added. The reaction mixture was stirred at 60° C. for 2 h. An aq solution of NaOH (1 M) was added to adjust the pH to 12. The solvents were removed under reduced pressure and the residue was purified by preparative HPLC on a C8 column using a gradient of 5-45% MeCN in water, MeCN and FA (95/5/0.2) buffer. $^1$H NMR (500 MHz, MeOH-$d_4$) δ 4.40 (s, 2H), 5.75 (s, 2H), 6.15 (d, 1H), 6.97 (d, 1H), 7.31 (d, 1H), 7.34 (dd, 1H), 7.53 (d, 1H). MS (APCI+) m/z 321 [M+H]$^+$.

Example 7, Alternative Preparation

1-[2-(Aminomethyl)-4-chlorobenzyl]-2-thioxo-1,2,3,5-tetrahydro-4H-pyrrolo[3,2-d]pyrimidin-4-one

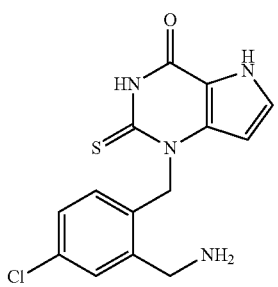 [SMILES: NCc1cc(Cl)ccc1Cn1c(=S)[nH]c(=O)c2[nH]ccc21]

A suspension of 5-chloro-2-[(4-oxo-2-thioxo-2,3,4,5-tetrahydro-1H-pyrrolo[3,2-d]pyrimidin-1-yl)methyl]benzaldehyde (see Example 6(e)) (500 g) and hydroxylamine hydrochloride (88.1 g, 1.1 eq) in DMF (5000 mL) was heated at 50° C. for 3 h. The reaction was cooled to 18-25° C. overnight and the solvent was removed in vacuo (maximum water bath temperature 55° C.) and water (7500 mL) was added to the residue. 1 M NaOH (aq) was then added to the suspension to adjust the pH to 10 (2000 mL used). After stirring for 1 h, the solid was filtered, washed with water (2×1785 mL) and pulled dry. Further drying in a vacuum oven at 45° C. yielded the intermediate oxime as a white solid (395.0 g). To a suspension of combined batches of this material (450.7 g) in acetic acid (6760 mL) at 18-25° C., zinc (50 g) was added. The reaction was then warmed to 50-60° C. Additional zinc (830.3 g, total added 880.3 g, 10 eq) was added portion-wise at 50-60° C. The reaction was stirred at 50° C. for 18 h. The reaction was filtered (hot) and the filtrate concentrated in vacuo (maximum water bath temperature 55° C.). The resulting solid was slurried in 20% HCl (aq, 3755 mL) for 1 h at 18-25° C. then filtered, washed with 20% HCl (aq, 1500 mL) then water (2×1500 mL) and pulled dry. The solid was then taken up in water (9014 mL) and MeCN (3155 mL). The pH was adjusted to 9-10 by the addition of 1 M NaOH (aq, 1120 mL). The thick suspension was stirred for 30 min and the solid filtered, washed with water (2×1300 mL) and pulled dry. Further drying in a vacuum oven at 45° C. yielded a white solid (390.9 g, 91%). Combined batches of this material (1098.1 g) were dissolved in DMSO (5490 mL) at 100-105° C. The solution was cooled to 70-80° C. and polish filtered to a second vessel. The temperature of the solution was adjusted to 75-80° C. and EtOH (6560 mL) was added drop-wise at 75-80° C. over 1 h (crystallisation occurred during addition). The suspension was stirred at 70° C. for 14 h before cooling to 18-25° C. at a rate of 10° C./h then stirred for 1 h. The solid was filtered, washed with ethanol (4×3660 mL) and pulled dry. Further drying in a vacuum oven yielded the title compound as an off-white solid (870 g). A suspension of (635.6 g) of this material in water (9534 mL)/MeCN (3432 mL) was acidified to pH 1 with 2 M aqHCl (1907 mL). After stirring at 18-25° C. for 1 h, the solid was filtered, washed with water (3180 mL then 2×1990 mL) and pulled dry. The wet cake was suspended in water (9534 mL)/EtOH (3432 mL) and the pH adjusted to 9-10 (monitored with pH meter) by the addition of 1 M aq NaOH (~2 L). The suspension was stirred at 18-25° C. for 1 h maintaining the pH at 9-10 as required (using 1 M aq NaOH). The solid was filtered, washed with water (3150 mL then 2×1574 mL) and pulled dry. Further drying in a vacuum oven at 45° C. yielded the title compound as white crystals (533.9 g). $^1$H NMR (500 MHz, MeOH-$d_4$) δ 4.40 (s, 2H), 5.75 (s, 2H), 6.15 (d, 1H), 6.97 (d, 1H), 7.31 (d, 1H), 7.34 (dd, 1H), 7.53 (d, 1H). MS (APCI+) m/z 321 [M+H]$^+$. LC indicated a purity of 98.4% with no single impurity >0.5%. Karl Fischer titration indicated 1.19% water.

Figure 5:
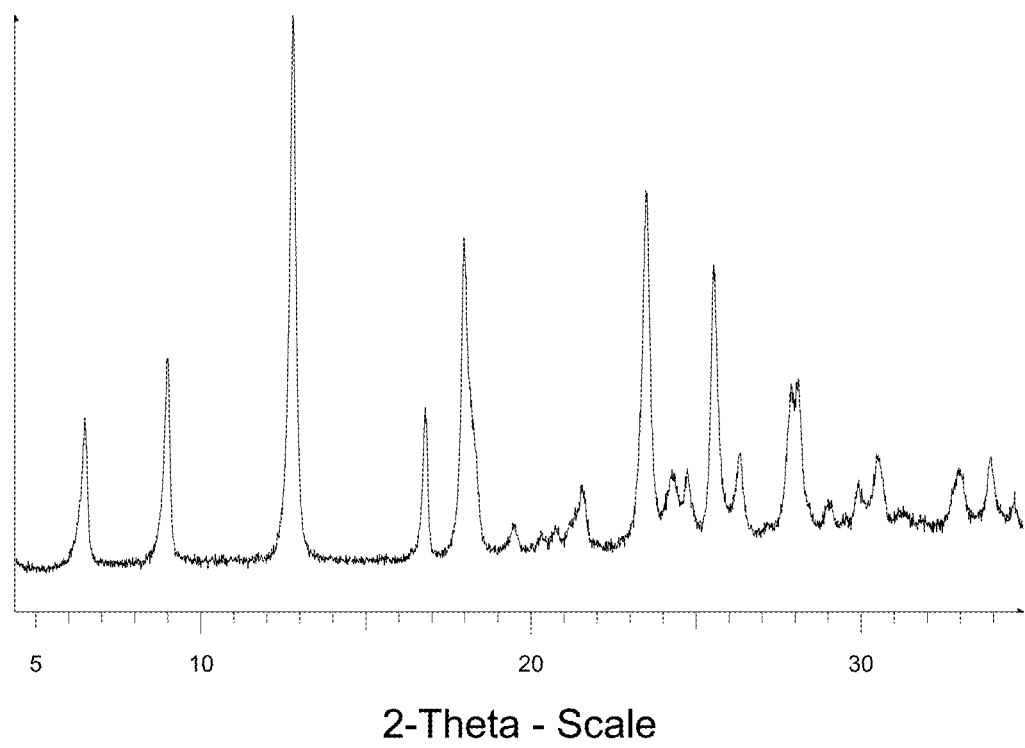
FIG. 5 shows the X-ray powder diffraction pattern for Example 7: 1-[2-(Aminomethyl)-4-chlorobenzyl]-2-thioxo-1,2,3,5-tetrahydro-4H-pyrrolo[3,2-d]pyrimidin-4-one.

The solid residue was found to be crystalline by XRPD and a typical diffractogranm is displayed in FIG. 5. Characteristic peak positions are listed below.

XRPD pattern 2-Theta (°) 6.5 (m), 9.0 (m), 12.8 (vs), 16.8 (m), 18.0 (s), 23.5 (s), 25.6 (s), 26.3 (w), 30.5 (w), 34.0 (w).

Example 8

1-{4-Chloro-2-[(methylamino)methyl]benzyl}-2-thioxo-1,2,3,5-tetrahydro-4H-pyrrolo[3,2-d]pyrimidin-4-one

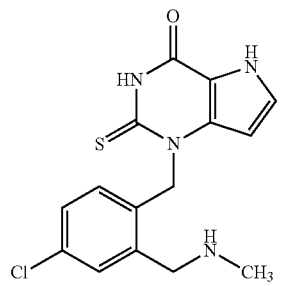 [SMILES: CNCc1cc(Cl)ccc1Cn1c(=S)[nH]c(=O)c2[nH]ccc21]

A mixture of 5-chloro-2-[(4-oxo-2-thioxo-2,3,4,5-tetrahydro-1H-pyrrolo[3,2-d]pyrimidin-1-yl)methyl]benzaldehyde (see Example 6(e))(1.00 g, 3.13 mmol) and methanamine (20 mL, 40.00 mmol) was heated in a microwave oven at 100° C. for 20 min. The mixture was diluted with MeOH and stirred at r.t. whereupon sodium tetrahydroborate (0.95 g, 25 mmol) was added in portions during 5 min. After stirring at r.t. for 1 h, the mixture was heated to reflux for 2 h. Another portion of sodium tetrahydroborate (0.47 g, 12.5 mmol) was added and the mixture was refluxed for additional 15 min. The solvent was removed by evaporation and to the residue was added water (20 mL) and an aq solution of HCl (1 M, 10 mL) to adjust the pH to 1. The mixture was cooled with an ice-bath and the formed precipitate was filtered off and washed with water (100 mL). The filtrate was cooled with an ice-bath and and the pH adjusted to pH 9 using an aq $NH_3$ solution (12%, 6 mL). A precipitate was isolated by filtration. After drying in vacuum, there was obtained 700 mg (67%) of the desired product as a white solid. $^1$H NMR (400 MHz, DMSO-$d_6$): δ 2.34 (d, 3H), 3.78 (s, 2H), 5.72 (s, 2H), 6.04 (t, 1H), 6.66 (d, 1H), 7.16 (dd, 1H), 7.27 (d, 1H), 7.41 (d, 1H). MS (APCI+) m/z 335 [M+H]$^+$.

Example 9

1-(2-{[(Cyclobutylmethyl)amino]methyl}benzyl)-2-thioxo-1,2,3,5-tetrahydro-4H-pyrrolo[3,2-d]pyrimidin-4-one

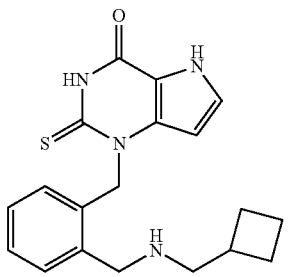 [SMILES: O=c1[nH]c(=S)n(Cc2ccccc2CNCC2CCC2)c2cc[nH]c12]

(a) Ethyl 3-{[2-(1,3-dioxolan-2-yl)benzyl]amino}-1H-pyrrole-2-carboxylate

A solution of ethyl 3-amino-1H-pyrrole-2-carboxylate hydrochloride (5.66 g, 29.69 mmol) in EtOH (30 mL) was treated with DIPEA (6.22 mL, 35.63 mmol) and stirred for 10 min before the addition of HOAc (4.08 mL, 71.25 mmol) and sodium cyanoborohydride (2.80 g, 44.53 mmol). A solution of 2-(1,3-dioxolan-2-yl)benzaldehyde (5.29 g, 29.69 mmol) in EtOH (20 mL) was then added dropwise over a period of 15 min. The resultant suspension was stirred at r.t. overnight. The reaction mixture was evaporated in vacuo and the residue treated with water (200 mL) and extracted with dichloromethane (3×150 mL). The organic solution was filtered through a silica gel column using a gradient of EtOAc and $CH_2Cl_2$ (0-100% EtOAc). There was obtained 12.63 g of the title compound as a crude product.

(b) Ethyl 3-{(benzoylcarbamothioyl([2-(1,3-dioxolan-2-yl)benzyl]amino}-1H-pyrrole-2-carboxylate Ethyl 3-{[2-(1,3-dioxolan-2-yl)benzyl]amino}-1H-pyrrole-2-carboxylate (12.63 g, 39.92 mmol) was suspended in $CH_2Cl_2$ (60 mL) and the suspension treated with DIPEA (7.09 mL, 39.92 mmol). The mixture was stirred for 0.25 h at r.t. and then benzoyl isothiocyanate (5.37 mL, 39.92 mmol) was added. After stirring for 18 h, the solvent was removed in vacuo. There was obtained 24.8 g of a crude title compound that was used without purification in the next step.

(c) 1-[2-(1,3-Dioxolan-2-yl)benzyl]-2-thioxo-1,2,3,5-tetrahydro-4H-pyrrolo[3,2-d]pyrimidin-4-one Ethyl 3-{(benzoylcarbamothioyl)[2-(1,3-dioxolan-2-yl)benzyl]amino}-1H-pyrrole-2-carboxylate (24.8 g, 51.72 mmol) was dissolved in MeOH (100 mL) and the solution treated with sodium hydroxide (10.34 g, 258.6 mmol). The mixture was heated to gentle reflux and stirred for 3.5 h. After cooling, the solvent was removed in vacuo. The residue was taken up in water, neutralised using HCl (2 M) and the mixture extracted with $CH_2Cl_2$ (3×50 mL). The combined extracts were washed with water (2×30 mL), dried (MgSO$_4$), filtered and evaporated. The residue was stirred with Et$_2$O and the precipitate was collected and dried to under vacuum. There was obtained 1.2 g (12.3% over 3 steps) of the title compound. MS (APCI+) m/z 330 [M+H]$^+$.

(d) 2-[4-Oxo-2-thioxo-2,3,4,5-tetrahydro-1H-pyrrolo[3,2-d]pyrimidin-1-yl)methyl]benzaldehyde To a solution of 1-[2-(1,3-dioxolan-2-yl)benzyl]-2-thioxo-1,2,3,5-tetrahydro-4H-pyrrolo[3,2-d]pyrimidin-4-one (1.2 g, 3.64 mmol) was added a solution of TFA (5.0 mL, 64.90 mmol) in $CH_2Cl_2$ (30 mL) and the mixture was stirred over night. The reaction mixture was refluxed for 7 h and then concentrated under vacuum. Toluene was added to co-evaporate the TFA. The dried crude was stirred with Et$_2$O to triturate the product which was collected via filtration and dried under vacuum. There was obtained 1.02 g (98%) of the title compound as a solid. MS (APCI+) m/z 286 [M+H]$^+$.

(e) 1-(2-{[(Cyclobutylmethyl)amino]methyl}benzyl)-2-thioxo-1,2,3,5-tetrahydro-4H-pyrrolo[3,2-d]pyrimidin-4-one A solution of 2-[(4-oxo-2-thioxo-2,3,4,5-tetrahydro-1H-pyrrolo[3,2-d]pyrimidin-1-yl)methyl]benzaldehyde (100 mg, 0.35 mmol), DIEA (0.184 mL, 1.05 mmol) and cyclobutylmethanamine (128 mg, 1.05 mmol) in dry NMP (3 mL) was stirred for 60 min then treated with sodium borohydride (19.89 mg, 0.53 mmol) and stirred at r.t. for 30 min. The solution was adsorbed by gravity onto a 10 g SCX column preswollen in NMP and the column then washed with MeOH (100 mL). The crude product was eluted using a solution of $NH_3$ in MeOH (3 M, 50 mL). The solvent was removed in vacuo and the residue was purified on a C8 column eluting with a gradient of MeOH in water (0.1% TFA). The product was slurried in dichloromethane (2 mL) to give 48 mg (38%) of the desire compound as a solid. $^1$H NMR (400 MHz, DMSO-$d_6$): δ 1.70-3.20 (m, 9H), 4.35 (m, 2H), 5.78 (s, 2H), 6.06 (m, 1H), 6.78 (d, 1H), 7.29 (t, 1H), 7.35 (m, 2H), 7.54 (d, 1H), 8.8 (b, 2H). MS (APCI+) m/z 355 [M+H]$^+$.

Example 10

1-{2-[(Cyclobutylamino)methyl]benzyl}-2-thioxo-1,2,3,5-tetrahydro-4H-pyrrolo[3,2-d]pyrimidin-4-one

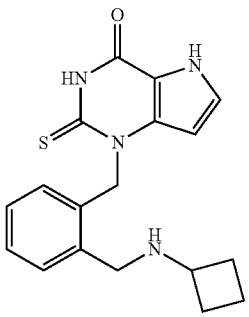 [SMILES: O=c1[nH]c(=S)n(Cc2ccccc2CNC2CCC2)c2cc[nH]c12]

The title compound was obtained as a solid in 49% yield starting from 2-[(4-oxo-2-thioxo-2,3,4,5-tetrahydro-1H-pyrrolo[3,2-d]pyrimidin-1-yl)methyl]benzaldehyde (100 mg, 0.35 mmol) and cyclobutanamine (249 mg, 3.50 mmol) using the procedure described in Example 9. $^1$H NMR (400 MHz, DMSO-$d_6$) δ 1.74-1.94 (m, 2H), 2.17-2.30 (m, 4H), 3.88 (s, 1H), 4.26 (s, 2H), 5.78 (s, 2H), 6.04 (t, 1H), 6.77 (d, 1H), 7.26-7.39 (m, 3H), 7.52 (dd, 1H), 9.09 (s, 2H), 12.41 (s, 1H), 12.52 (s, 1H). MS (APCI+) m/z 341 [M+H]$^+$.

Example 11

1-{2-[(Cyclopentylamino)methyl]benzyl}-2-thioxo-1,2,3,5-tetrahydro-4H-pyrrolo[3,2-d]pyrimidin-4-one

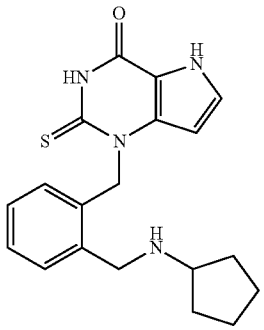 [SMILES: O=c1[nH]c(=S)n(Cc2ccccc2CNC2CCCC2)c2cc[nH]c12]

The title compound was obtained as a solid in 54% yield starting from 2-[(4-oxo-2-thioxo-2,3,4,5-tetrahydro-1H-pyrrolo[3,2-d]pyrimidin-1-yl)methyl]benzaldehyde (100 mg, 0.35 mmol) and cyclopentanamine (0.35 mL, 3.50 mmol) using the procedure described in Example 9. $^1$H NMR (400 MHz, DMSO-$d_6$): δ1.40-2.80 (m, 8H), 3.70 (m, 1H), 4.37 (m, 1H), 5.79 (s, 2H), 6.04 (t, 1H), 6.79 (d, 1H), 7.20-7.40 (m, 3H), 7.54 (d, 1H) 8.85 (b, 2H). MS (APCI+) m/z 355 [M+H]$^+$.

Example 12

1-(2-{[(2-Methylpropyl)amino]methyl}benzyl)-2-thioxo-1,2,3,5-tetrahydro-4H-pyrrolo[3,2-d]pyrimidin-4-one

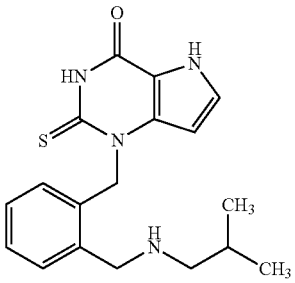 [SMILES: CC(C)CNCc1ccccc1Cn1c(=S)[nH]c(=O)c2[nH]ccc21]

The title compound was obtained as a solid in 71% yield starting from 2-[(4-oxo-2-thioxo-2,3,4,5-tetrahydro-1H-pyrrolo[3,2-d]pyrimidin-1-yl)methyl]benzaldehyde (100 mg, 0.35 mmol) and 2-methylpropan-1-amine (0.35 mL, 3.50 mmol) using the procedure described in Example 9. $^1$H NMR (400 MHz, DMSO-$d_6$): δ 1.00 (d, 6H), 2.05 (m, 1H), 2.95 (m, 2H), 4.40 (m, 2H), 5.79 (s, 1H), 6.06 (dd, 1H), 6.78 (d, 1H), 7.28 (t, 1H), 7.36 (m, 2H), 7.58 (dd, 1H), 8.78 (b, 2H). MS (APCI+) m/z 343 [M+H]$^+$.

Example 13

1-{2-[(Propan-2-ylamino)methyl]benzyl}-2-thioxo-1,2,3,5-tetrahydro-4H-pyrrolo[3,2-d]pyrimidin-4-one

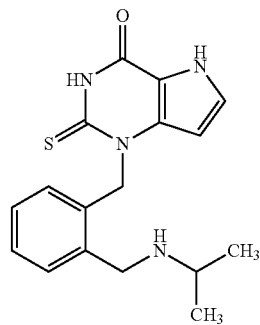 [SMILES: CC(C)NCc1ccccc1Cn1c(=S)[nH]c(=O)c2[nH]ccc21]

The title compound was obtained as a solid in 33% yield starting from 2-[(4-oxo-2-thioxo-2,3,4,5-tetrahydro-1H-pyrrolo[3,2-d]pyrimidin-1-yl)methyl]benzaldehyde (100 mg, 0.35 mmol) and 2-methylpropan-1-amine propan-2-amine (0.45 mL, 5.61 mmol) using the procedure described in Example 9. $^1$H NMR (400 MHz, DMSO-$d_6$): δ 1.36 (d, 6H), 3.55 (m, 1H), 4.39 (m, 2H), 5.79 (s, 1H), 6.05 (d, 1H), 6.78 (d, 1H), 7.27 (t, 1H), 7.36 (m, 2H), 7.54 (dd, 1H), 8.76 (b, 2H). MS (APCI+) m/z 329 [M+H]$^+$.

Example 14

1-[2-(Aminomethyl)-4-(trifluoromethyl)benzyl]-2-thioxo-1,2,3,5-tetrahydro-4H-pyrrolo[3,2-d]pyrimidin-4-one

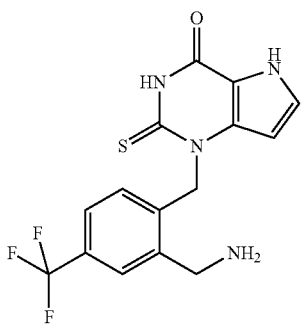 [SMILES: NCc1cc(C(F)(F)F)ccc1Cn1c(=S)[nH]c(=O)c2[nH]ccc21]

(a) 1-Bromo-2-(diethoxymethyl)-4-(trifluoromethyl)benzene

A solution of 2-bromo-5-(trifluoromethyl)benzaldehyde (0.60 mL, 3.95 mmol), triethyl orthoformate (1.316 mL, 7.90 mmol) and tetrabutylammonium tribromide (0.019 g, 0.04 mmol) in EtOH (99.5%, 6 mL) was stirred at r.t. for 8 h. Additional triethyl orthoformate (1.32 mL, 7.90 mmol) and tetrabutylammonium tribromide (0.019 g, 0.04 mmol) were added and the reaction mixture was stirred for additionally 15 h.

The solvent was removed under reduced pressure and to the residue were added an aq solution of sat. NaHCO$_3$ and EtOAc. The layers were separated and the aq phase was extracted twice with EtOAc. The combined organic layers were washed with brine, dried with a phase separator and the solvent was removed under reduced pressure to result in 0.94 g (72%) of the title compound. $^1$H NMR (500 MHz, CDCl$_3$): δ 1.27 (t, 6H), 3.58-3.73 (m, 4H), 5.67 (s, 1H), 7.45 (dd, 1H), 7.69 (d, 1H), 7.93 (d, 1H).

(b) 2-(Diethoxymethyl)-4-(trifluoromethyl)benzaldehyde

Butyllithium (2.5 M in hexane, 15.47 mL, 38.67 mmol) was added dropwise to a solution of 1-bromo-2-(diethoxymethyl)-4-(trifluoromethyl)benzene (11.5 g, 35.15 mmol) in THF (130 mL) at −78° C. under a nitrogen atmosphere and the resulting solution was stirred at −78° C. for 30 min. DMF (4.06 mL, 52.73 mmol) was added dropwise at −78° C. The reaction mixture was allowed to warm to r.t. and stirred for 2 h. An aq solution of sat. NH$_4$Cl was added and the phases were separated. The aq layer was extracted twice with EtOAc. The combined organic layers were washed with brine, dried (phase separator) and the solvents were removed under reduced pressure. There was obtained 9.0 g (33%) of the title compound.

(C) Ethyl 3-{[2-(diethoxymethyl-4-(trifluoromethyl)benzyl]amino}-1H-pyrrole-2-carboxylate Ethyl 3-amino-1H-pyrrole-2-carboxylate (5.02 g, 32.58 mmol) was dissolved in EtOH (99.5%, 110 mL) and to the resultant solution was added DIPEA (5.67 mL, 32.58 mmol) followed by HOAc (3.73 mL, 65.16 mmol). The reaction mixture was cooled to −10° C. and then sodium cyanotrihydroborate (2.46 g, 39.09 mmol) was added. 2-(Diethoxymethyl)-4-(trifluoromethyl)benzaldehyde (9 g, 32.58 mmol) dissolved in EtOH (99.5%, 10 mL) was then added slowly. The reaction mixture was stirred at 0° C. and then stirred for 16 h, during which the temperature was allowed to increase to r.t. Water was added and the mixture extracted with toluene. The aq phase was further extracted twice with toluene and the combined organic layers were washed with brine, dried through a phase separator and the solvent was removed under reduced pressure. The product was purified by preparative HPLC using a C8 column and using a mixture comprising a gradient (50%-100%) MeCN in water, MeCN and ammonium acetate buffer (0.1 M). After four injections, there was obtained 4.5 g (33%) of the title compound. $^1$H NMR (500 MHz, CDCl$_3$): δ 1.25 (td, 4H), 1.34 (t, 3H), 3.51-3.7 (m, 5H), 4.31 (dd, 2H), 4.57 (s, 2H), 5.60 (dd, 1H), 5.66 (s, 1H), 6.68 (s, 1H), 7.53 (d, 1H), 7.58 (d, 1H), 7.85 (s, 1H), 8.09 (d, 1H). MS (APCI+) m/z 414 [M+H]$^+$.

(d) 1-[2-(Diethoxymethyl)-4-(trifluoromethyl)benzyl]-2-thioxo-1,2,3,5-tetrahydro-4H-pyrrolo[3,2-d]pyrimidin-4-one Ethyl 3-{[2-(diethoxymethyl)-4-(trifluoromethyl)benzyl]amino}-1H-pyrrole-2-carboxylate (4.3 g, 10.38 mmol) was dissolved in MeOH (40 mL) and to the resultant solution was added benzoyl isothiocyanate (1.40 mL, 10.38 mmol). The reaction mixture was stirred at r.t. for 15 min and then Cs$_2$CO$_3$ (7.27 g, 22.31 mmol) was added. The mixture was stirred at 60° C. for 6 h and then the solvent was removed under reduced pressure. Water and dichloromethane were added and the aq phase was further extracted trice with CH$_2$Cl$_2$. The organic layers were combined and the solvent was removed under reduced pressure. The residue was triturated with Et$_2$O. The formed suspension was stirred for 4 h and the solid isolated by filtration. The solids were washed with Et$_2$O to give 3.46 g (78%) of the title compound. $^1$H NMR (500 MHz, DMSO-d$_6$): δ 1.22 (t, 6H), 3.55-3.72 (m, 4H), 5.89 (s, 3H), 5.95 (s, 1H), 6.94 (d, 1H), 7.24 (s, 1H), 7.59 (d, 1H), 7.83 (s, 1H), 12.38 (s, 2H). MS (APCI−) m/z 426 [M−H]$^-$.

(e) 2-[(4-Oxo-2-thioxo-2,3,4,5-tetrahydro-1H-pyrrolo[3,2-d]pyrimidin-1-yl)methyl]-5-(trifluoromethyl)benzaldehyde A mixture of TFA (2.90 mL, 39.07 mmol) and CH$_2$Cl$_2$ (12 mL) was cooled to 0° C. and to the solution was added 1-(2-(diethoxymethyl)-4-(trifluoromethyl)benzyl)-2-thioxo-2,3-dihydro-1H-pyrrolo[3,2-d]pyrimidin-4(5H)-one (1.67 g, 3.91 mmol). The ice-bath was removed and the mixture was stirred at r.t. for 2.5 h. The resulting solid was filtered and washed with CH$_2$Cl$_2$ to result in 1.31 g (95%) of the title compound. $^1$H NMR (500 MHz, DMSO-d$_6$): δ 6.09-6.16 (m, 3H), 7.08 (d, 1H), 7.31 (t, 1H), 7.89 (dd, 1H), 8.41 (d, 1H), 10.34 (s, 1H), 12.44 (s, 1H), 12.52 (s, 1H). MS (APCI+) m/z 352 [M−H]$^-$.

(f) 1-[2-(Aminomethyl)-4-(trifluoromethyl)benzyl]-2-thioxo-1,2,3,5-tetrahydro-4H-pyrrolo[3,2-d]pyrimidin-4-one 2-[(4-Oxo-2-thioxo-2,3,4,5-tetrahydro-1H-pyrrolo[3,2-d]pyrimidin-1-yl)methyl]-5-(trifluoromethyl)benzaldehyde (195 mg, 0.55 mmol) was added to a mixture of hydroxylamine hydrochloride (42 mg, 0.61 mmol) in HOAc (80%, 4 mL). The mixture was stirred at r.t. for 1 h and zinc (181 mg, 2.76 mmol) was added. After stirring at 60° C. for 1.5 h, the mixture was cooled and the pH adjusted to 12 with aq NaOH (1 M). The resulting precipitate was collected by filtration. The product was purified by preparative HPLC on a C8 column using a gradient of 5-45% MeCN in water, MeCN and FA (95/5/0.2). There was obtained 70 mg (36%) of the desired compound. $^1$H NMR (500 MHz, DMSO-d$_6$): δ 4.37 (s, 2H), 5.81 (s, 2H), 6.11 (s, 1H), 6.93 (d, 1H), 7.36 (s, 1H), 7.63 (d, 1H), 7.89 (s, 1H), 8.36 (s, 2H), 12.47 (s, 1H), 12.56 (s, 1H).

Example 15

1-{2-[(Methylamino)methyl]-4-(trifluoromethyl)benzyl}-2-thioxo-1,2,3,5-tetrahydro-4H-pyrrolo[3,2-d]pyrimidin-4-one

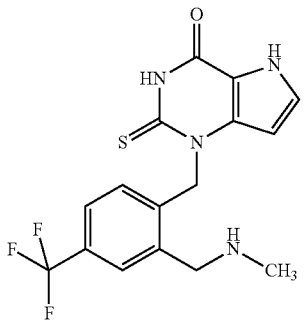 [SMILES: CNCc1cc(C(F)(F)F)ccc1Cn1c(=S)[nH]c(=O)c2[nH]ccc21]

2-[(4-Oxo-2-thioxo-2,3,4,5-tetrahydro-1H-pyrrolo[3,2-d]pyrimidin-1-yl)methyl]-5-(trifluoromethyl)benzaldehyde (214 mg, 0.61 mmol) and methanamine (2 M in MeOH, 3.03 mL, 6.06 mmol) were dissolved in MeOH (5 mL) and the resulting solution was transferred to a microwave vial. The reaction mixture was heated at 100° C. for 5 min and then diluted with THF (5 mL). Sodium tetrahydroborate (183 mg, 4.85 mmol) was added in small portions during 2 min. The reaction mixture was stirred at r.t. for 30 min and then quenched by the addition of water. The solvents were evaporated and the crude product was purified by preparative HPLC on a C18 column using a gradient of 15-55% MeCN in water, MCN and 0.1 M NH$_4$OAc buffer (95/5/0.2), then re-purified using a gradient of 0-30% MeCN in water, MeCN and FA (95/5/0.2). There was obtained 62 mg (28%) of the title compound. $^1$H NMR (500 MHz, DMSO-d$_6$) δ 2.42 (s, 3H), 3.94 (s, 2H), 5.85 (s, 2H), 6.10 (d, 1H), 6.88 (d, 1H), 7.32 (d, 1H), 7.51 (d, 1H), 7.76 (s, 1H), 8.19 (s, 1H). MS (APCI+) m/z 369 [M+H]$^+$.

What is claimed is:

1. A method of treating cardiovascular disease chosen from coronary artery disease, acute coronary syndrome, heart failure, chronic kidney disease (CKD), cardiorenal syndrome (CRS), non-alcoholic steatohepatitis (NASH), and arrhythmia in a patient in need thereof, comprising:

a) identifying a patient with elevated plasma urate levels; and
b) administering an MPO inhibitor to the patient;
wherein the MPO inhibitor is chosen from 1-{2-[(1R)-1-aminoethyl]-4-chlorobenzyl}-2-thioxo-1,2,3,5-tetrahydro-4H-pyrrolo[3,2-d]pyrimidin-4-one

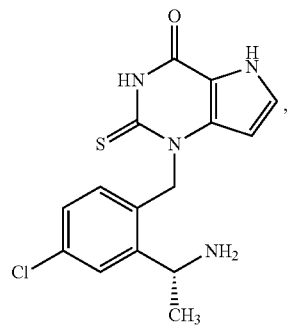 [SMILES: C[C@@H](N)c1cc(Cl)ccc1Cn1c(=S)[nH]c(=O)c2[nH]ccc21]

or a pharmaceutically acceptable salt thereof; or 1-[2-(aminomethyl)-4-chlorobenzyl]-2-thioxo-1,2,3,5-tetrahydro-4H-pyrrolo[3,2-d]pyrimidin-4-one:

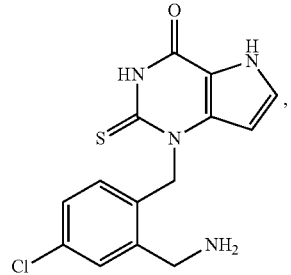 [SMILES: NCc1cc(Cl)ccc1Cn1c(=S)[nH]c(=O)c2[nH]ccc21]

or a pharmaceutically acceptable salt thereof.

2. A method of treating cardiovascular disease HF with preserved ejection fraction (HFpEF) in a patient in need thereof, comprising administering an MPO inhibitor to the patient, wherein the patient has elevated plasma urate levels, wherein the MPO inhibitor is 1-{2-[(1R)-1-aminoethyl]-4-chlorobenzyl}-2-thioxo-1,2,3,5-tetrahydro-4H-pyrrolo [3,2-d]pyrimidin-4-one

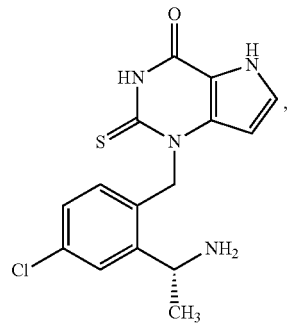 [SMILES: C[C@@H](N)c1cc(Cl)ccc1Cn1c(=S)[nH]c(=O)c2[nH]ccc21]

or a pharmaceutically acceptable salt thereof; or 1-[2-(aminomethyl)-4-chlorobenzyl]-2-thioxo-1,2,3,5-tetrahydro-4H-pyrrolo[3,2-d]pyrimidin-4-one:

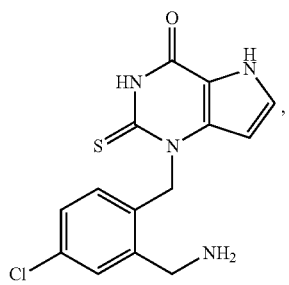 [SMILES: NCc1cc(Cl)ccc1Cn1c(=S)[nH]c(=O)c2[nH]ccc21]
or a pharmaceutically acceptable salt thereof.
\* \* \* \* \*